United States Patent
Limon et al.

(10) Patent No.: US 10,684,191 B2
(45) Date of Patent: Jun. 16, 2020

(54) APPARATUS, SYSTEM AND METHOD OF DETERMINING ONE OR MORE OPTICAL PARAMETERS OF A LENS

(71) Applicant: 6 OVER 6 VISION LTD., Kfar Saba (IL)

(72) Inventors: Ofer Limon, Kfar Saba (IL); Haim Bachar, Tel Aviv (IL); Nir Altmark, Tel Aviv (IL); Shahar Levy, Rishon LeZion (IL)

(73) Assignee: 6 OVER 6 VISION LTD., Kfar Saba (IL)

( * ) Notice: Subject to any disclaimer, the term of this patent is extended or adjusted under 35 U.S.C. 154(b) by 88 days.

(21) Appl. No.: 15/572,920

(22) PCT Filed: May 10, 2016

(86) PCT No.: PCT/IB2016/052673
§ 371 (c)(1),
(2) Date: Nov. 9, 2017

(87) PCT Pub. No.: WO2016/181310
PCT Pub. Date: Nov. 17, 2016

(65) Prior Publication Data
US 2018/0140182 A1    May 24, 2018

Related U.S. Application Data

(60) Provisional application No. 62/286,331, filed on Jan. 23, 2016, provisional application No. 62/216,757, (Continued)

(51) Int. Cl.
*G01M 11/02* (2006.01)
*A61B 3/02* (2006.01)
(Continued)

(52) U.S. Cl.
CPC ........... *G01M 11/0228* (2013.01); *A61B 3/02* (2013.01); *G01M 11/0221* (2013.01);
(Continued)

(58) Field of Classification Search
CPC ......... G01M 11/0228; G01M 11/0235; G01M 11/0264; G01M 11/0221; G06T 7/00;
(Continued)

(56) References Cited

U.S. PATENT DOCUMENTS

| | | |
|---|---|---|
| 3,880,525 A | 4/1975 | Johnson |
| 4,070,115 A | 1/1978 | Humphrey |

(Continued)

FOREIGN PATENT DOCUMENTS

| | | |
|---|---|---|
| CN | 101561347 | 10/2009 |
| CN | 101842683 | 9/2010 |

(Continued)

OTHER PUBLICATIONS

International Preliminary Report on Patentability for PCT/IB2016/052672, dated Nov. 23, 2017, 6 pages.
(Continued)

*Primary Examiner* — William R Alexander
*Assistant Examiner* — Henry A Duong
(74) *Attorney, Agent, or Firm* — Shichrur & Co.

(57) ABSTRACT

Some demonstrative embodiments include apparatuses, systems and/or methods of determining one or more optical parameters of a lens of eyeglasses. For example, a product may include one or more tangible computer-readable non-transitory storage media including computer-executable instructions operable to, when executed by at least one computer processor, enable the at least one computer processor to implement operations of determining one or more optical parameters of a lens of eyeglasses. The operations may include processing at least one image of an object
(Continued)

captured via the lens; and determining the one or more optical parameters of the lens based on the at least one image.

30 Claims, 27 Drawing Sheets

Related U.S. Application Data filed on Sep. 10, 2015, provisional application No. 62/159,295, filed on May 10, 2015.

(51) Int. Cl.
*G02C 7/02* (2006.01)
*G02C 13/00* (2006.01)
*G06T 7/00* (2017.01)

(52) U.S. Cl.
CPC .... *G01M 11/0235* (2013.01); *G01M 11/0264* (2013.01); *G02C 7/02* (2013.01); *G02C 13/003* (2013.01); *G06T 7/00* (2013.01)

(58) Field of Classification Search
CPC .......... G02C 13/003; G02C 7/02; A61B 3/02; A61B 3/102; A61B 3/1025; A61B 3/103
USPC ........................................................ 351/205
See application file for complete search history.

(56) References Cited

U.S. PATENT DOCUMENTS

| | | | |
|---|---|---|---|
| 4,611,913 | A | 9/1986 | Sugino |
| 5,331,394 | A | 7/1994 | Shalon et al. |
| 5,396,324 | A | 3/1995 | Kurachi et al. |
| 5,855,074 | A | 1/1999 | Abitbol et al. |
| 5,971,537 | A | 10/1999 | Fukuma et al. |
| 5,973,772 | A | 10/1999 | Fukuma et al. |
| 6,061,123 | A | 5/2000 | Ikezawa et al. |
| 6,349,145 | B1 | 2/2002 | Nakayama et al. |
| 9,813,693 | B1 | 11/2017 | Baldwin |
| 9,835,519 | B2 | 12/2017 | Meng |
| 2001/0055111 | A1 | 12/2001 | Yoda et al. |
| 2005/0068495 | A1* | 3/2005 | Jojiki ...................... A61B 3/111 351/204 |
| 2005/0190360 | A1* | 9/2005 | Kajino ................ G01M 11/0207 356/124 |
| 2006/0152709 | A1 | 7/2006 | Imaizumi |
| 2010/0220285 | A1* | 9/2010 | Simmonds ........... G02C 13/005 351/204 |
| 2013/0016222 | A1 | 1/2013 | Jiang et al. |
| 2013/0155393 | A1 | 6/2013 | Blonde et al. |
| 2014/0300726 | A1 | 10/2014 | Gladnick |
| 2015/0070650 | A1* | 3/2015 | Seriani ................. A61B 3/0025 351/204 |
| 2015/0109577 | A1 | 4/2015 | Haddadi et al. |
| 2015/0139534 | A1 | 5/2015 | Komatsu |
| 2015/0330865 | A1* | 11/2015 | Meng ................. G01M 11/0228 356/124 |
| 2016/0202498 | A1 | 7/2016 | Ozaki et al. |
| 2016/0299360 | A1 | 10/2016 | Fonte et al. |
| 2016/0309992 | A1 | 10/2016 | Stith et al. |
| 2016/0327779 | A1 | 11/2016 | Hillman |
| 2017/0111630 | A1 | 4/2017 | Geiss et al. |
| 2018/0038768 | A1 | 2/2018 | Hofmann et al. |
| 2018/0106700 | A1 | 4/2018 | Limon et al. |
| 2018/0140182 | A1 | 5/2018 | Limon et al. |
| 2019/0072455 | A1 | 3/2019 | Limon et al. |
| 2019/0368970 | A1 | 12/2019 | Limon et al. |

FOREIGN PATENT DOCUMENTS

| | | |
|---|---|---|
| CN | 103163663 | 6/2013 |
| CN | 103217273 | 7/2013 |
| CN | 203132816 | 8/2013 |
| CN | 103412415 | 11/2013 |
| DE | 19646360 | 5/1998 |
| DE | 10341161 | 2/2005 |
| DE | 102007057260 | 6/2009 |
| EP | 1679499 | 7/2006 |
| EP | 2608109 | 6/2013 |
| JP | S50-145249 | 11/1975 |
| JP | S58-139044 | 8/1983 |
| JP | S58156828 | 9/1983 |
| JP | S59-67440 | 4/1984 |
| JP | 09243514 | 9/1997 |
| JP | 2001-21449 | 1/2001 |
| JP | 2006-189386 | 7/2006 |
| JP | 2011-209530 | 10/2011 |
| JP | 2013-127621 | 6/2013 |
| JP | 2015-025859 | 2/2015 |
| KR | 20060093596 | 8/2006 |
| KR | 101528132 | 6/2015 |
| WO | 97/25647 | 7/1997 |
| WO | 2015051573 | 4/2015 |
| WO | 2016141333 | 9/2016 |

OTHER PUBLICATIONS

International Search Report and Written Opinion for PCT/IB2016/052672, dated Sep. 11, 2016, 8 pages.
International Preliminary Report on Patentability for PCT /IB2016/052673, dated Nov. 23, 2017, 8 pages.
International Search Report and Written Opinion for PCT/IB2016/052673, dated Aug. 29, 2016, 12 pages.
International Search Report and Written Opinion for PCT/IB2017/050338, dated Jun. 14, 2017, 14 pages.
European Search Report for European Patent Application No. 16792278.0, dated Jan. 7, 2019, 19 pages.
European Search Report for European Patent Application No. 16792277.2, dated Jan. 2, 2019, 23 pages.
Office Action for Chinese Patent Application No. 201680040517.0, dated Mar. 29, 2019, 35 pages (Including 20 pages of English translation).
European Search Report for European Patent Application No. 16792277.2, dated Apr. 3, 2019, 22 pages.
European Search Report for European Patent Application No. 16792278.0, dated Apr. 9, 2019, 18 pages.
Office Action for Russian Patent Application No. 2017139574/28, dated Apr. 25, 2019, 17 pages (Including 8 pages of English translation).
Notice of Allowance for U.S. Appl. No. 15/572,893, dated May 13, 2019, 9 Pages.
Office Action for U.S. Appl. No. 15/572,893, dated Oct. 22, 2018, 18 pages.
Office Action for Russian Patent Application No. 2017139574, dated Dec. 24, 2018, 15 pages (Including 7 pages of English translation).
Office Action for U.S. Appl. No. 15/572,893, dated Mar. 18, 2019, 26 pages.
Office Action for Chinese Patent Application No. 201680040458.7, dated Nov. 14, 2019, 35 pages (Including 20 pages of English translation).
Ru Zheng et al., "A device for detecting progressive addition lenses", Optical Technique, vol. 41, Issue 4, chaps.1-3, Jul. 2015, 3 pages.
European Search Report for European Patent Application No. 17741169.1, dated Sep. 12, 2019, 8 pages.
Office Action for Russian Patent Application No. 2017139576 dated Sep. 26, 2019, 16 pages (Including 8 pages of English translation).
Notice of Allowance for U.S. Appl. No. 15/767,205, dated Oct. 23, 2019, 14 Pages.
Notice of Allowance for U.S. Appl. No. 15/572,893, dated Nov. 5, 2019, 12 Pages.
Notice of Allowance for U.S. Appl. No. 15/767,205, dated Jun. 25, 2019, 36 Pages.

(56) References Cited

OTHER PUBLICATIONS

Office Action for Chinese Patent Application No. 201680040517.0, dated Nov. 4, 2019, 33 pages (Including 21 pages of English translation).
Office Action for Japanese Patent Application No. 2017-558641, dated Mar. 17, 2020, 11 pages [including 6 pages of English translation].
Office Action for Chinese Patent Application No. 201780018306.1, dated Feb. 3, 2020, 7 pages.
Office Action for U.S. Appl. No. 16/539,142, dated Apr. 9, 2020, 36 pages.
Office Action for Japanese Patent Application No. 2017-558737, dated Mar. 24, 2020, 10 pages [including 5 pages of English translation].

* cited by examiner

APPARATUS, SYSTEM AND METHOD OF DETERMINING ONE OR MORE OPTICAL PARAMETERS OF A LENS

CROSS REFERENCE

This Application claims the benefit of and priority from U.S. Provisional Patent Application No. 62/159,295 entitled "APPARATUS, SYSTEM AND METHOD OF DETERMINING ONE OR MORE OPTICAL PARAMETERS OF A LENS", filed May 10, 2015, U.S. Provisional Patent Application No. 62/216,757 entitled "APPARATUS, SYSTEM AND METHOD OF DETERMINING ONE OR MORE OPTICAL PARAMETERS OF A LENS", filed Sep. 10, 2015, and U.S. Provisional Patent Application No. 62/286,331 entitled "APPARATUS, SYSTEM AND METHOD OF DETERMINING ONE OR MORE OPTICAL PARAMETERS OF A LENS", filed Jan. 23, 2016, the entire disclosures of all of which are incorporated herein by reference.

TECHNICAL FIELD

Embodiments described herein generally relate to determining one or more optical parameters of a lens.

BACKGROUND

Eyeglasses and/or prescription eyeglasses may include lenses assembled in a frame of the eyeglasses.

The lenses may have one or more optical parameters. The optical parameters of a lens may include, for example, a spherical power, a cylindrical power and/or a cylindrical axis.

Determining the spherical power, the cylindrical power, and/or the cylindrical axis of the lens may be useful, for example, if a user of the eyeglasses wishes to duplicate the eyeglasses and/or to produce spare lenses for the eyeglasses.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

DETAILED DESCRIPTION

Figure 1:
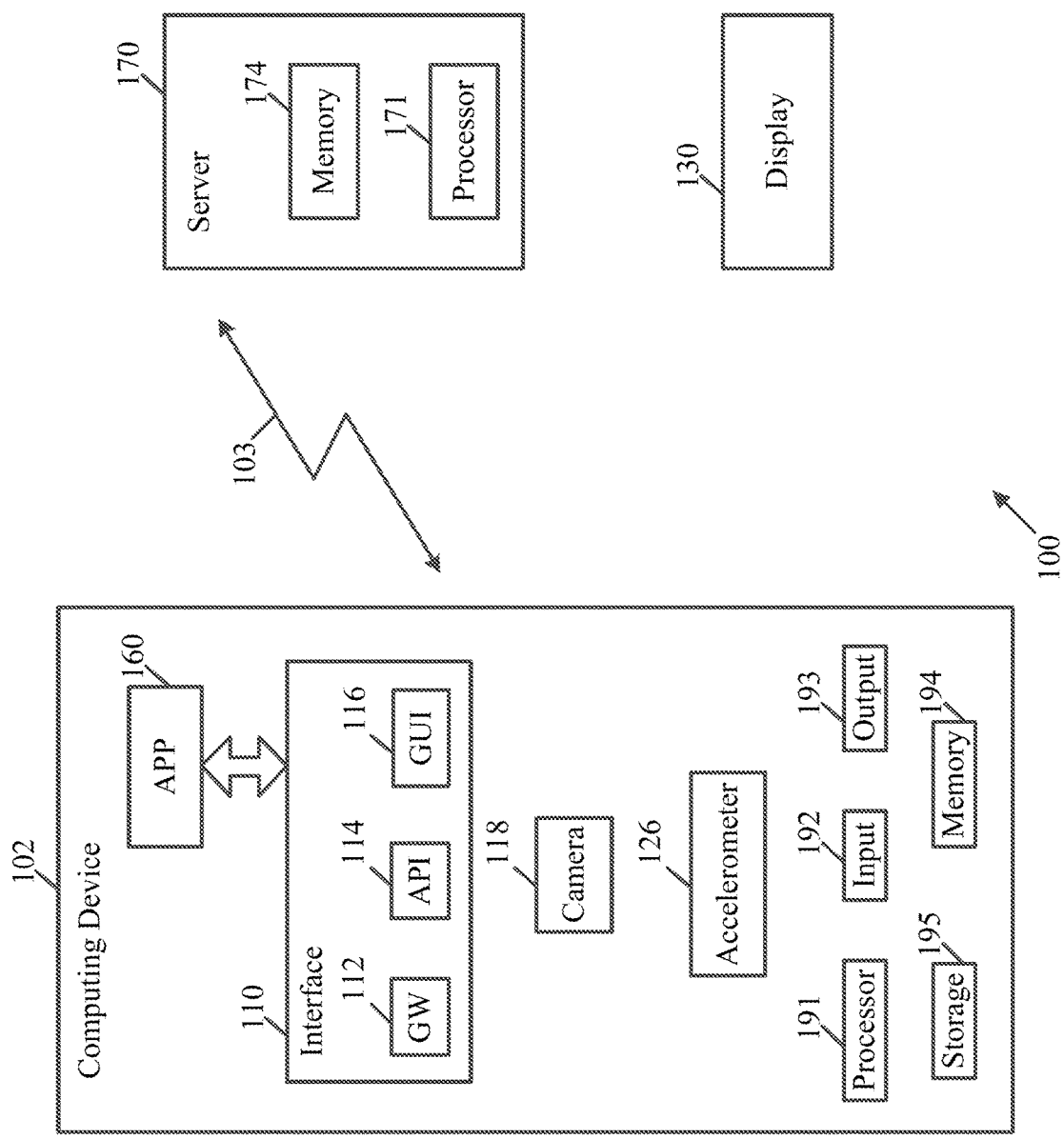
FIG. 1 is a schematic block diagram illustration of a system, in accordance with some demonstrative embodiments.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Some portions of the following detailed description are presented in terms of algorithms and symbolic representations of operations on data bits or binary digital signals within a computer memory. These algorithmic descriptions and representations may be the techniques used by those skilled in the data processing arts to convey the substance of their work to others skilled in the art.

An algorithm is here, and generally, considered to be a self-consistent sequence of acts or operations leading to a desired result. These include physical manipulations of physical quantities. Usually, though not necessarily, these quantities capture the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Discussions herein utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments" etc., indicate that the embodiment(s) so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified the use of the ordinal adjectives "first", "second", "third" etc., to describe a common object, merely indicate that different instances of like objects are being referred to, and are not intended to imply that the objects so described must be in a given sequence, either temporally, spatially, in ranking, or in any other manner.

Some embodiments, for example, may capture the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments may capture the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some demonstrative embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a FLASH memory, a rigid magnetic disk, and an optical disk. Some demonstrative examples of optical disks include compact disk-read only memory (CD-ROM), compact disk-read/write (CD-R/W), and DVD.

In some demonstrative embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some demonstrative embodiments, input/output or I/O devices (including but not limited to keyboards, displays, pointing devices, etc.) may be coupled to the system either directly or through intervening I/O controllers. In some demonstrative embodiments, network adapters may be coupled to the system to enable the data processing system to become coupled to other data processing systems or remote printers or storage devices, for example, through intervening private or public networks. In some demonstrative embodiments, modems, cable modems and Ethernet cards are demonstrative examples of types of network adapters. Other suitable components may be used.

Some embodiments may include one or more wired or wireless links, may utilize one or more components of wireless communication, may utilize one or more methods or protocols of wireless communication, or the like. Some embodiments may utilize wired communication and/or wireless communication.

Some embodiments may be used in conjunction with various devices and systems, for example, a mobile phone, a Smartphone, a mobile computer, a laptop computer, a notebook computer, a tablet computer, a handheld computer, a handheld device, a Personal Digital Assistant (PDA) device, a handheld PDA device, a mobile or portable device, a non-mobile or non-portable device, a cellular telephone, a wireless telephone, a device having one or more internal antennas and/or external antennas, a wireless handheld device, or the like.

Reference is now made to FIG. 1, which schematically illustrates a block diagram of a system 100, in accordance with some demonstrative embodiments.

As shown in FIG. 1, in some demonstrative embodiments system 100 may include a device 102.

In some demonstrative embodiments, device 102 may be implemented using suitable hardware components and/or software components, for example, processors, controllers, memory units, storage units, input units, output units, communication units, operating systems, applications, or the like.

In some demonstrative embodiments, device 102 may include, for example, a computing device, a mobile phone, a Smartphone, a Cellular phone, a notebook, a mobile computer, a laptop computer, a notebook computer, a tablet computer, a handheld computer, a handheld device, a PDA device, a handheld PDA device, a wireless communication device, a PDA device which incorporates a wireless communication device, or the like.

In some demonstrative embodiments, device 102 may include, for example, one or more of a processor 191, an input unit 192, an output unit 193, a memory unit 194, and/or a storage unit 195. Device 102 may optionally include other suitable hardware components and/or software components. In some demonstrative embodiments, some or all of the components of one or more of device 102 may be enclosed in a common housing or packaging, and may be interconnected or operably associated using one or more wired or wireless links. In other embodiments, components of one or more of device 102 may be distributed among multiple or separate devices.

In some demonstrative embodiments, processor 191 may include, for example, a Central Processing Unit (CPU), a Digital Signal Processor (DSP), one or more processor cores, a single-core processor, a dual-core processor, a multiple-core processor, a microprocessor, a host processor, a controller, a plurality of processors or controllers, a chip, a microchip, one or more circuits, circuitry, a logic unit, an Integrated Circuit (IC), an Application-Specific IC (ASIC), or any other suitable multi-purpose or specific processor or controller. Processor 191 may execute instructions, for example, of an Operating System (OS) of device 102 and/or of one or more suitable applications.

In some demonstrative embodiments, input unit 192 may include, for example, a keyboard, a keypad, a mouse, a touch-screen, a touch-pad, a track-ball, a stylus, a microphone, or other suitable pointing device or input device. Output unit 193 may include, for example, a monitor, a screen, a touch-screen, a flat panel display, a Light Emitting Diode (LED) display unit, a Liquid Crystal Display (LCD) display unit, a plasma display unit, one or more audio speakers or earphones, or other suitable output devices.

In some demonstrative embodiments, memory unit 194 includes, for example, a Random Access Memory (RAM), a Read Only Memory (ROM), a Dynamic RAM (DRAM), a Synchronous DRAM (SD-RAM), a flash memory, a volatile memory, a non-volatile memory, a cache memory, a buffer, a short term memory unit, a long term memory unit, or other suitable memory units. Storage unit 195 may include, for example, a hard disk drive, a floppy disk drive, a Compact Disk (CD) drive, a CD-ROM drive, a DVD drive, or other suitable removable or non-removable storage units. Memory unit 194 and/or storage unit 195, for example, may store data processed by device 102.

In some demonstrative embodiments, device 102 may be configured to communicate with one or more other devices via a wireless and/or wired network 103.

In some demonstrative embodiments, network 103 may include a wired network, a local area network (LAN), a wireless LAN (WLAN) network, a radio network, a cellular network, a Wireless Fidelity (WiFi) network, an IR network, a Bluetooth (BT) network, and the like.

In some demonstrative embodiments, device 102 may allow one or more users to interact with one or more processes, applications and/or modules of device 102, e.g., as described herein.

In some demonstrative embodiments, device 102 may be configured to perform and/or to execute one or more operations, modules, processes, procedures and/or the like.

In some demonstrative embodiments, device 102 may be configured to determine a one or more optical parameters of a lens of eyeglasses, e.g., provided by a user of device 102, e.g., as described below.

In some demonstrative embodiments, system 100 may be configured to perform lensmeter or lensometer analysis of the lens of the eyeglasses, for example, even without using any auxiliary optical means, e.g., as described below.

In some demonstrative embodiments, the one or more optical parameters of the lens may include a spherical power, a cylindrical power and/or a cylindrical axis of the lens.

In some demonstrative embodiments, system 100 may be configured to analyze a focal power of a spherical lens, a focal power and an axis of a cylindrical lens, and/or a distance between the centers of two lenses assembled in a frame of the eyeglasses, e.g., as described below.

In some demonstrative embodiments, system 100 may include at least one service, module, controller, and/or application 160 configured to determine the one or more optical parameters of the lens provided by the user of device 102, e.g., as described below.

In some demonstrative embodiments, application 160 may include, or may be implemented as, software, a software module, an application, a program, a subroutine, instructions, an instruction set, computing code, words, values, symbols, and the like.

In some demonstrative embodiments, application 160 may include a local application to be executed by device 102. For example, memory unit 194 and/or storage unit 195 may store instructions resulting in application 160, and/or processor 191 may be configured to execute the instructions resulting in application 160, e.g., as described below.

In other embodiments, application 160 may include a remote application to be executed by any suitable computing system, e.g., a server 170.

In some demonstrative embodiments, server 170 may include at least a remote server, a web-based server, a cloud server, and/or any other server.

In some demonstrative embodiments, the server 170 may include a suitable memory and/or storage unit 174 having stored thereon instructions resulting in application 160, and a suitable processor 171 to execute the instructions, e.g., as descried below.

In some demonstrative embodiments, application 160 may include a combination of a remote application and a local application.

In one example, application 160 may be downloaded and/or received by the user of device 102 from another computing system, e.g., server 170, such that application 160 may be executed locally by users of device 102. For example, the instructions may be received and stored, e.g., temporarily, in a memory or any suitable short-term memory or buffer of device 102, e.g., prior to being executed by processor 191 of device 102.

In another example, application 160 may include a frontend to be executed locally by device 102, and a backend to be executed by server 170. For example, one or more first operations of determining the one or more optical parameters of the lens of the user may be performed locally, for example, by device 102, and/or one or more second operations of determining the one or more optical parameters may be performed remotely, for example, by server 170, e.g., as described below.

In other embodiments, application 160 may include any other suitable computing arrangement and/or scheme.

In some demonstrative embodiments, system 100 may include an interface 110 to interface between a user of device 102 and one or more elements of system 100, e.g., application 160.

In some demonstrative embodiments, interface 110 may be implemented using any suitable hardware components and/or software components, for example, processors, controllers, memory units, storage units, input units, output units, communication units, operating systems, and/or applications.

In some embodiments, interface 110 may be implemented as part of any suitable module, system, device, or component of system 100.

In other embodiments, interface 110 may be implemented as a separate element of system 100.

In some demonstrative embodiments, interface 110 may be implemented as part of device 102. For example, interface 110 may be associated with and/or included as part of device 102.

In one example, interface 110 may be implemented, for example, as middleware, and/or as part of any suitable application of device 102. For example, interface 110 may be implemented as part of application 160 and/or as part of an OS of device 102.

In some demonstrative embodiments, interface 160 may be implemented as part of server 170. For example, interface 110 may be associated with and/or included as part of server 170.

In one example, interface 110 may include, or may be part of a Web-based application, a web-site, a web-page, a plug-in, an ActiveX control, a rich content component (e.g., a Flash or Shockwave component), or the like.

In some demonstrative embodiments, interface 110 may be associated with and/or may include, for example, a gateway (GW) 112 and/or an application programming interface (API) 114, for example, to communicate information and/or communications between elements of system 100 and/or to one or more other, e.g., internal or external, parties, users, applications and/or systems.

In some embodiments, interface 110 may include any suitable Graphic-User-Interface (GUI) 116 and/or any other suitable interface.

In some demonstrative embodiments, system 100 may include a display 130 configured to display one or more objects to be captured by an image capturing device, and/or to display information, objects, instructions and/or any other content, for example, to a user, e.g., as described below.

In some demonstrative embodiments, display 130 may include a separate display, a stand-alone display and/or a display device, e.g., separate from other elements of system 100.

In some demonstrative embodiments, display 130 may be part of device 102 or part of server 170.

In some demonstrative embodiments, display 130 may be part of any other computing system, e.g., a laptop, a desktop, and/or the like.

In some demonstrative embodiments, display 130 may include, for example, a monitor, a screen, a touch-screen, a flat panel display, a LED display unit, an LCD display unit, a plasma display unit, one or more audio speakers or earphones, and/or any other suitable components.

In some demonstrative embodiments, the GUI 116 of interface 110 may be displayed on display 130.

In some demonstrative embodiments, application 160 may be configured to determine the one or more optical parameters of the lens, for example, based on at least one captured image of an object, e.g., as described below.

In some demonstrative embodiments, the object may include an object having one or more known dimensions, e.g., as described below.

In some demonstrative embodiments, application 160 may be configured to determine the one or more optical parameters of the lens, for example, based on the dimensions of the object, e.g., as described below.

In some demonstrative embodiments, the object may include a circularly symmetric or rotationally symmetric object, e.g., as described below.

In some demonstrative embodiments, the object may be displayed on display 130.

In other embodiments, the object may include an object which is not displayed on display 130, e.g., the object may include a physical object, which may be placed, presented, and/or positioned, for example, to enable device 102 to capture the image of the object, e.g., as described below.

In some demonstrative embodiments, application 160 may be configured to control, cause, trigger, and/or instruct display 130 to display the object.

In some demonstrative embodiments, application 160 may be configured to calibrate a display size of the object on display 130, e.g., as described below.

In some demonstrative embodiments, the captured image may be captured by the user, and may include the object, e.g., as described below.

In some demonstrative embodiments, the captured image of the object may be captured via the lens of the eyeglasses.

In some demonstrative embodiments, device 102 may include an image capturing device, e.g., a camera 118 or any other device, configured to capture the at least one image.

In some demonstrative embodiments, application 160 may be configured to control, cause, trigger, and/or instruct camera 118 to capture the at least one image including the object.

In some demonstrative embodiments, application 160 may be configured to instruct the user to capture at least one image of the object via the lens of the eyeglasses.

In some demonstrative embodiments, application 160 may be configured to control, cause, trigger, and/or instruct camera 118 to capture the at least one image via the center of the lens, or via any other part of the lens.

In some demonstrative embodiments, an image of the object, as may be seen by the camera 118, e.g., through the lens, may be magnified and/or deformed, for example, if the lens includes a spherical lens and/or a cylindrical lens, e.g., as described below.

In some demonstrative embodiments, the magnification and/or deformation of the image may vary, for example, according to the spherical power, the cylindrical axis and/or the cylindrical power of the lens.

In some demonstrative embodiments, application 160 may be configured to determine the one or more optical parameters of the lens based on the magnification and/or deformation of the image captured via the lens, e.g., as described below.

In some demonstrative embodiments, application 160 may be configured to receive the at least one image of the object captured via the lens of the eyeglasses, e.g., directly or indirectly from the camera 118.

In one example, application 160 may be configured to determine the one or more optical parameters of the lens locally, for example, if application 160 is locally implemented by device 102. According to this example, camera 118 may be configured to capture the image, and application 160 may be configured to receive the captured image, e.g., from camera 118, and to determine the one or more optical parameters of the lens, e.g., as described below.

In another example, application 160 may be configured to determine the one or more optical parameters of the lens remotely, for example, if application 160 is implemented by server 170, or if the back-end of application 160 is implemented by server 170, e.g., while the front-end of application 160 is implemented by device 102. According to this example, camera 118 may be configured to capture the image; the front-end of application 160 may be configured to receive the captured image; and server 170 and/or the back-end of application 160 may be configured to determine the one or more optical parameters of the lens, e.g., based on information received from the front-end of application 160.

In one example, device 102 and/or the front-end of application 160 may be configured to send the captured image and, optionally, additional information, e.g., as described below, to server 170, e.g., via network 103; and/or server 170 and/or the back-end of application 160 may be configured to receive the captured image, and to determine the one or more optical parameters of the lens, for example, based on the captured image from device 102.

In some demonstrative embodiments, application 160 may be configured to determine the one or more optical parameters of the lens, for example, based on a magnification between at least one imaged dimension of the object in the image captured via the lens, and at least one respective reference dimension of the object, e.g., as described below.

In some demonstrative embodiments, application 160 may be configured to determine the one or more optical parameters of the lens, for example, based on a first distance ("the camera distance") between the object and camera 118 when the image is captured via the lens, and a second distance ("the lens distance") between the object and the lens of the eyeglasses ("the eyeglasses lens") when the image is capture via the lens.

In some demonstrative embodiments, application 160 may be configured to determine the one or more optical parameters of the lens, for example, based on the magnification, e.g., as described below.

demonstrative embodiments, application 160 may be configured to determine the one or more optical parameters of the lens, for example, based on the first and second distances, e.g., as described below.

In some demonstrative embodiments, the lens distance may be set to be, measured to be, approximated to be, and/or assumed to be, half of the camera distance, e.g., as described below.

In other embodiments, any other relationship between the first and second distances may be set, measured, approximated, and/or assumed, e.g., as described below.

In other embodiments, the first and/or second distances may be set and/or defined based on one or more measurements and/or based on one or more images captured via the lens, e.g., as described below.

Figure 2:
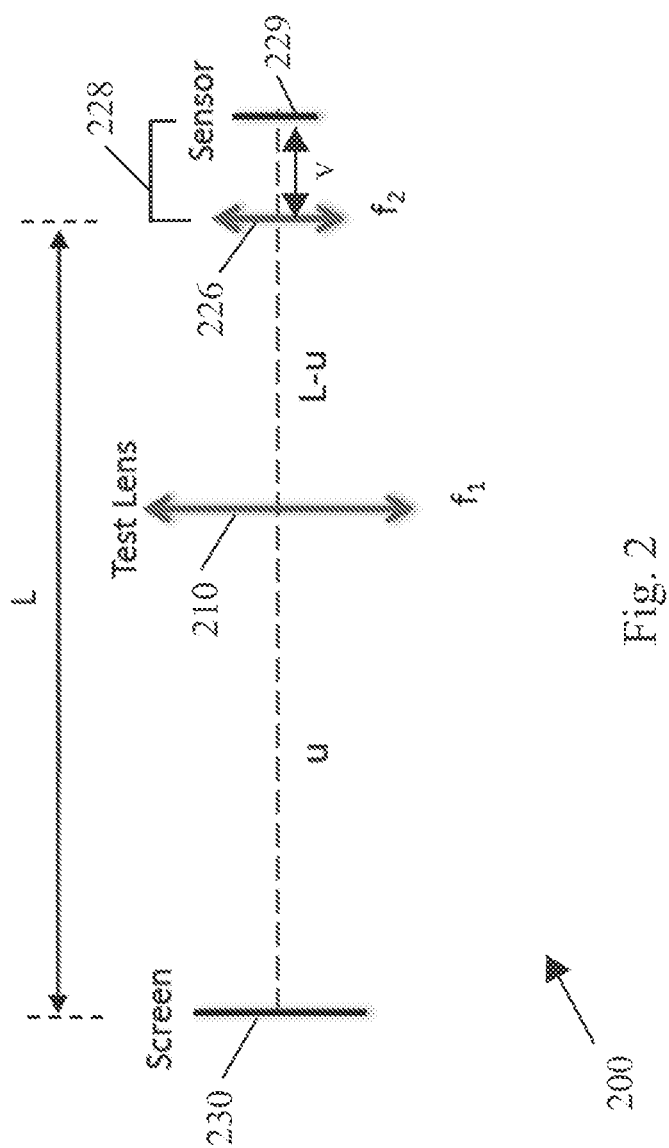
FIG. 2 is a schematic illustration of a measurement scheme, in accordance with some demonstrative embodiments.

Reference is made to FIG. 2, which schematically illustrates a measurement scheme 200, in accordance with some demonstrative embodiments. In one example, one or more elements of FIG. 1 may be arranged and/or operated according to the measurement scheme 200, one or more parameters may be determined be application 160 (FIG. 1) based on measurement scheme 200, and/or one or more measurements may be performed be one or more elements of FIG. 1 according to measurement scheme 200, e.g., as described below.

As shown in FIG. 2, measurement scheme 200 may include a display 230 to display an object, an eyeglasses lens 210 ("the lens"), a lens 228 ("the camera lens") of a camera 218, and/or a sensor 229 ("the camera sensor") of the camera 218. For example, display 230 may perform the functionality of display 130 (FIG. 1), and/or camera 218 may perform the functionality of camera 118 (FIG. 1).

As shown in FIG. 2, a camera distance, denoted L, may be between display 230 and the camera 218, e.g., the camera lens 228; a lens distance, denoted u, may be between the eyeglasses lens 210 and display 230; and/or a third distance, denoted v, may be between the camera lens 228 and the camera sensor 229.

As shown in FIG. 2, the lens 210 may have a focal length, denoted $f_1$, and/or the camera lens 228 may have a focal length, denoted $f_2$.

In some demonstrative embodiments, the following equations may be applied, for example, if the lens 210 includes a negative lens.

In some demonstrative embodiments, positive values for $f_1$ may be used, for example, if lens 210 include a negative lens, e.g., as described below.

In some demonstrative embodiments, negative values for $f_1$, e.g., $-f_1$ may be used, for example, if lens 210 includes a positive lens.

In some demonstrative embodiments, according to measurement scheme 200, one or more relationships may be applied, e.g., as follows:

$$\frac{1}{u} + \frac{1}{v} = \frac{1}{f_1} \tag{1}$$

$$v = \frac{f_1 u}{u - f_1}$$

$$M_1 \equiv \frac{v}{u} = \frac{f_1}{u - f_1}$$

In some demonstrative embodiments, sensor 229 may sense the object on the display 230 at a new location, denoted u', e.g., as follows:

$$u' = \frac{-f_1 u}{u - f_1} + (L - u) \tag{2}$$

In some demonstrative embodiments, a magnification, denoted $M_2$, of the camera lens 228, may be determined, e.g., as follows:

$$M_2 = \frac{f_2}{u' - f_2} = \frac{f_2}{\frac{-f_1 u}{u - f_1} + (L - u) - f_2} \tag{3}$$

In some demonstrative embodiments, a total magnification, denoted $M_T$, according to the measurement scheme 200 may be determined, e.g., as follows:

$$M_T = M_1 * M_2 = \tag{4}$$

$$\frac{f_2 f_1}{-f_1 u + (L - u)(u - f_1) - f_2(u - f_1)} = \frac{f_2 f_1}{Lu - Lf_1 - u^2 - f_2(u - f_1)}$$

wherein $M_1$ denotes a magnification of the lens 210.

In some demonstrative embodiments, the magnification, denoted $M_0$, at a location u=0 may be, e.g., as follows:

$$M_0 = \frac{f_2}{L - f_2} \tag{5}$$

In some demonstrative embodiments, the magnification $M_0$ may be equal to a magnification without the lens 210.

In some demonstrative embodiments, a relative magnification, denoted $M_R$, may be determined, e.g. as follows:

$$M_R = \frac{M_T}{M_0} = \frac{f_1(f_2 - L)}{L(u - f_1) - u^2 + f_2 f_1 - f_2 u} \quad (6)$$

In some demonstrative embodiments, a largest magnification of measurement scheme 200 may occur at a position, at which the relative magnification $M_R$ satisfies one or more conditions, e.g., as follows:

$$\frac{dM_R}{du} = 0 \quad (7)$$

$$\frac{dM_R}{du} = -\frac{f_1(f_2 - L)}{[L(u - f_1) - u^2 + f_2 f_1 - f_2 u]^2} * (L - 2u - f_2) = 0$$

In other embodiments, the largest magnification may occur at a position, denoted $u_{ideal}$, which satisfies, e.g., at least the following criterion:

$$\boxed{u_{ideal} = \frac{L - f_2}{2}} \quad (8)$$

In some demonstrative embodiments, since $L \gg f_2$ the best position for the largest magnification may be, e.g., approximately, at a middle between display 230 and the camera lens 228.

In some demonstrative embodiments, the relative magnification $M_R$, for example, at the position $u_{ideal}$, e.g., at the middle between display 230 and the camera lens 228, may be determined, e.g., as follows:

$$M_R(u = u_{ideal}) \approx \frac{f_1(L - f_2)}{L(0.5L - f_1) - 0.25L^2 + f_2 f_1 - 0.5 f_2 L} \quad (9)$$

In some demonstrative embodiments, a spherical power of lens 210 may be extracted for a given camera distance L, for example, by measuring the relative magnification $M_R$, e.g., preferably at the position $u_{ideal}$ peak, or at any other point.

In some demonstrative embodiments, if the lens 210 has a cylinder, the relative magnification formula, e.g., according to Equation 9, may be applied to each of the cylinder axes separately.

In some demonstrative embodiments, the distance U between the display 230 and the lens 210 may be determined, for example, using the magnification formula, e.g., according to Equation 9.

In some demonstrative embodiments, since the maximum magnification is given at the middle between display 230 and lens 228, capturing several images, when the lens 210 is located at different distances between display 230 and the camera lens 228, may enable evaluating the maximum magnification, for example, by fitting, extrapolating or sampling, and/or from a known/calculated/measured camera distance L of the camera from the display 230.

In some demonstrative embodiments, the focal length $f_1$ of lens 210 may be determined, for example, based on the total magnification $M_T$, and/or the relative magnification $M_R$, e.g., as follows:

$$f_1 = \frac{Lu - u^2 - f_2 u}{f_2 / M_T + L - f_2} \quad (10)$$

or $$f_1 = \frac{Lu - u^2 - f_2 u}{f_2 / M_R - L / M_R + L - f_2}$$

In some demonstrative embodiments, a focus of the camera 218 may be fixed, for example, on the distance of the camera to display 230.

In some demonstrative embodiments, the camera 218 may focus on display 230 and lock the focus, e.g., before inserting the lens 210 in front of camera 218.

In other embodiments, the focusing on display 230 may be performed, for example, after placing the lens 210, e.g., between display 230 and the camera 218, e.g., by focusing on the parts on display 230 that do not include the frame of the eyeglasses, e.g., including the lens 210, in the field of view (FOV) of the camera 218. For example, image processing techniques may be implemented to determine where in the FOV should the camera 218 perform the autofocus (AF).

In another embodiment, the area in the FOV of the camera 218 to perform the AF may be selected manually, for example, by instructing the user to select the area in the FOV of the camera 218, in which the camera may focus.

In some demonstrative embodiments, the magnification and the extraction of the focal power of lens 210 may be determined, for example, by focusing only on display 230.

In some demonstrative embodiments, camera 218 may be focused using the object on display 230, for example, without the lens 210, e.g., as follows:

$$v_s = \frac{L f_2}{L - f_2} \quad (11)$$

In some demonstrative embodiments, the lens 210 may form a virtual object located at the distance u' from camera lens, e.g., as follows:

$$u' = L - u + \frac{f_1 u}{f_1 + u} \quad (12)$$

In some demonstrative embodiments, the total magnification $M_T$ in the system may be determined, e.g., as follows:

$$M_T = M_1 M_2 = \frac{f_1}{f_1 + u} \times \frac{\frac{L f_2}{L - f_2}}{L - u + \frac{f_1 u}{f_1 + u}} \quad (13)$$

In some demonstrative embodiments, the focal length $f_1$ of the lens 210 may be determined, e.g., as follows:

$$f_1 = \frac{(L - u) M_T u}{\frac{L f_2}{L - f_2} - L M_T} \quad (14)$$

In some demonstrative embodiments, the power, denoted $P_1$, of the lens 210 may be determined, e.g., as follows:

$$P_1 = \frac{1}{f_1} \quad (15)$$

Figure 3:
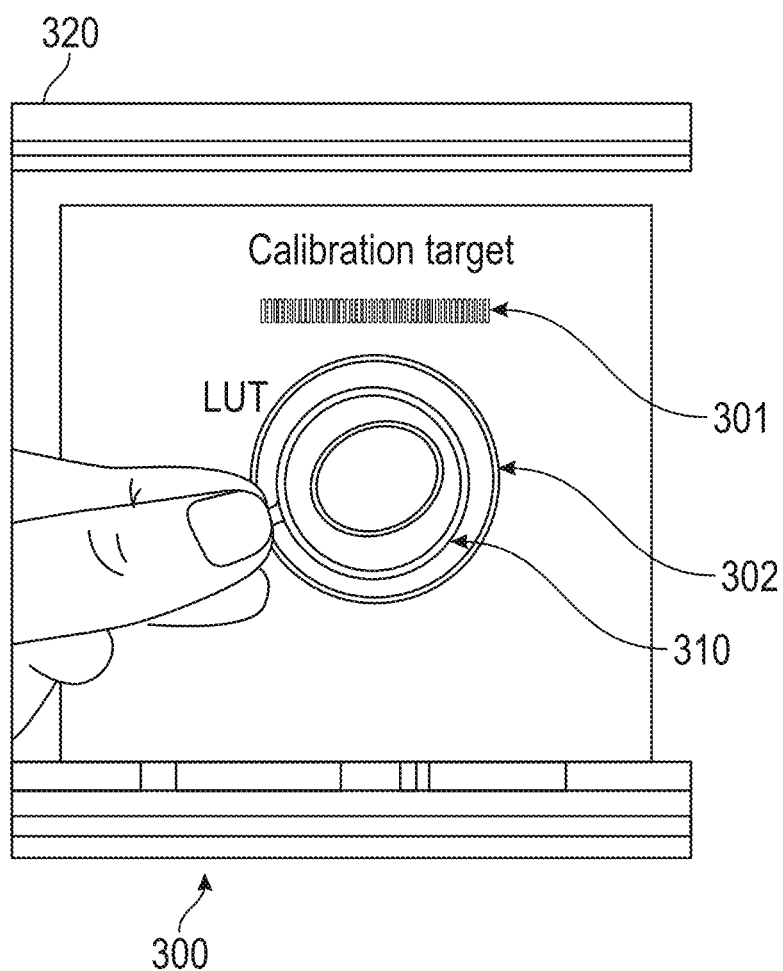
FIG. 3 is a schematic illustration of an image of an object displayed on a display, in accordance with some demonstrative embodiments.

Reference is made to FIG. 3, which schematically illustrates an image 300 of an object 302 displayed on a display 330. For example, display 330 may perform the functionality of display 130 (FIG. 1).

In some demonstrative embodiments, as shown in FIG. 3, object 302 may include a circle.

In some demonstrative embodiments, image 300 of object 302 may be captured by a camera via a lens 310. For example, camera 118 (FIG. 1) and/or camera 218 (FIG. 2) may capture object 302 via lens 310, e.g., lens 210 (FIG. 2).

As shown in FIG. 3, when image 300 of object 302 is captured through lens 310, lens 310 may change the magnification of object 302, e.g., in a different way for various angles.

As shown in FIG. 3, when an image of object 302 is captured through lens 310, image 300 may be seen as an ellipsoid.

In some demonstrative embodiments, the camera may be focused to a calibration object 301, which may be placed outside of the field of view of lens 310.

In some demonstrative embodiments, as shown in FIG. 3, lens 310 may not affect an image of the calibration object 301, e.g., since calibration object 301 is placed outside of the FOV of lens 310.

Reference is made to FIGS. 4A, 4B, and 4C and 4D which schematically illustrate four respective relative magnification graphs, in accordance with some demonstrative embodiments.

In one example, the camera distance L, e.g., between camera 218 (FIG. 2) and display 230 (FIG. 2), may be equal to 50 cm, and the focal length $f_2$, e.g., of lens 228 (FIG. 2), may be equal to 3.7 mm. In other embodiments, any other distances may be used.

In some demonstrative embodiments, the four graphs of FIGS. 4A, 4B, and 4C and 4D depict the relative magnification as a function of a distance of a lens, e.g., lens 210 (FIG. 2), from a camera sensor, e.g., sensor 229 (FIG. 2).

In some demonstrative embodiments, a graph of FIGS. 4A, 4B, and 4C and 4D depicts a plurality of magnification curves corresponding to a plurality of different lenses.

In some demonstrative embodiments, the plurality of different lenses may correspond to a plurality of diopter intervals within a certain range of diopters.

For example, a magnification curve may represent a magnification of a lens having a specific diopter from the certain range of diopters as a function of the distance of the lens from the camera.

Figure 4A:
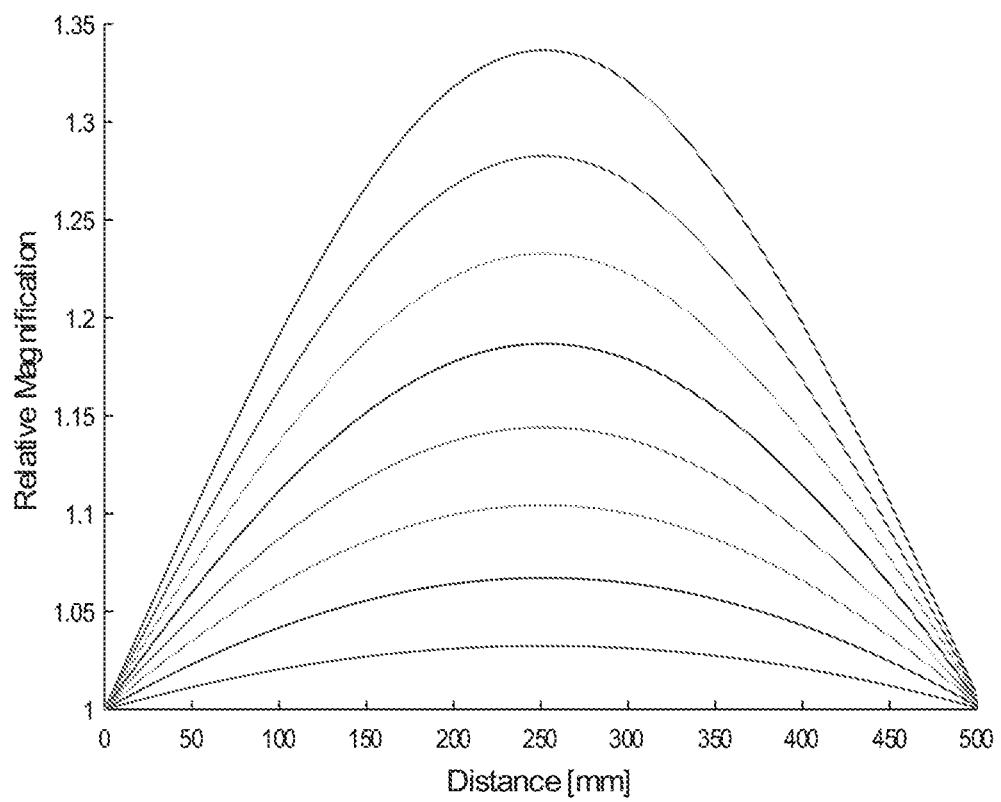
FIGS. 4A, 4B, and 4C and 4D are schematic illustrations of four respective relative magnification graphs, in accordance with some demonstrative embodiments.

In some demonstrative embodiments, the plurality of magnification curves of FIG. 4A may correspond to a plurality of lenses having a lens power of between 0.25 D and 2 D, at 0.25 diopter intervals.

Figure 4B:
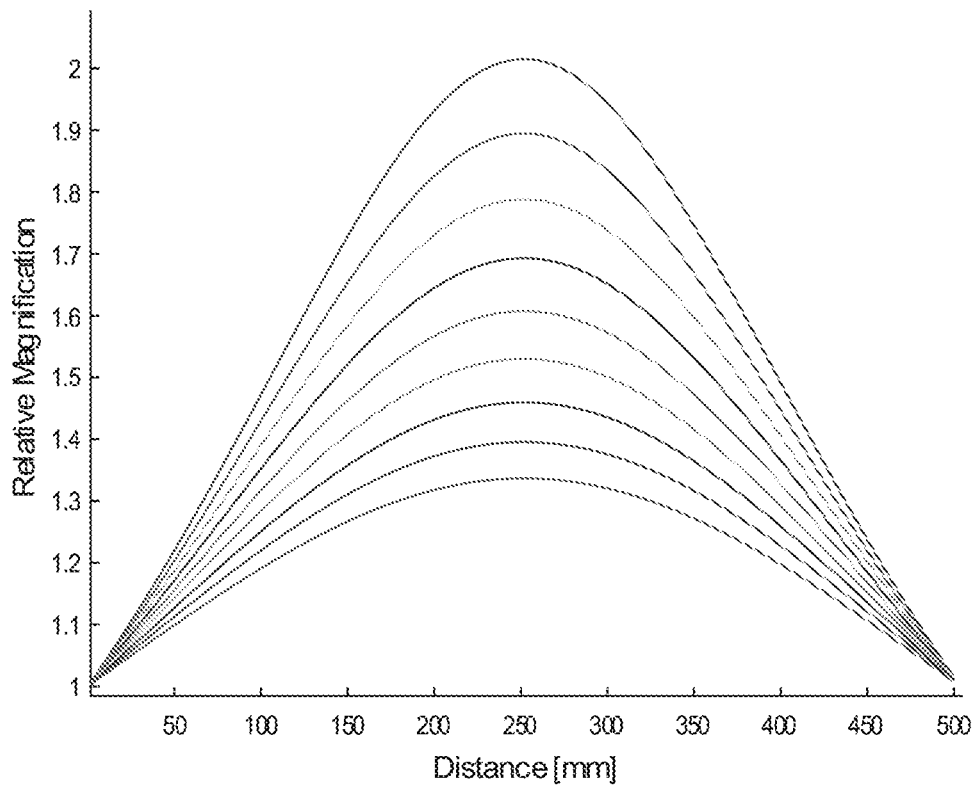

In some demonstrative embodiments, the plurality of magnification curves of FIG. 4B may correspond to a plurality of lenses having a lens power of between 2 D and 4 D, at 0.25 diopter intervals.

Figure 4C:
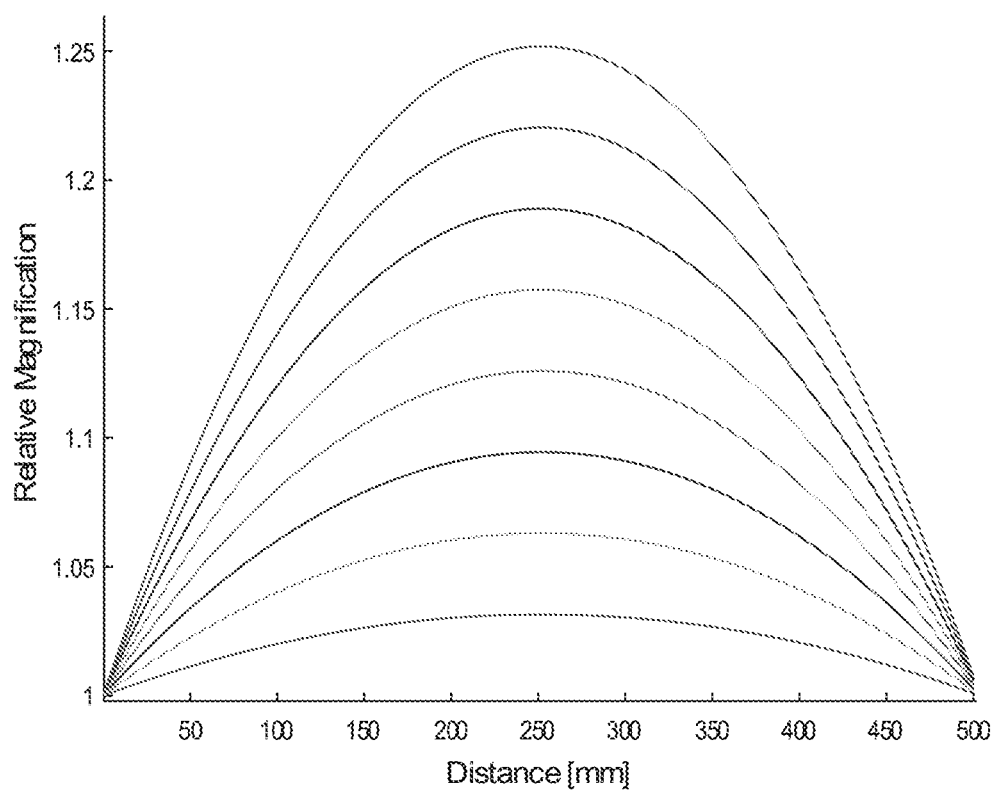

In some demonstrative embodiments, the plurality of magnification curves of FIG. 4C may correspond to a plurality of lenses having a lens power of between −0.25 D and −2 D, at 0.25 diopter intervals.

Figure 4D:
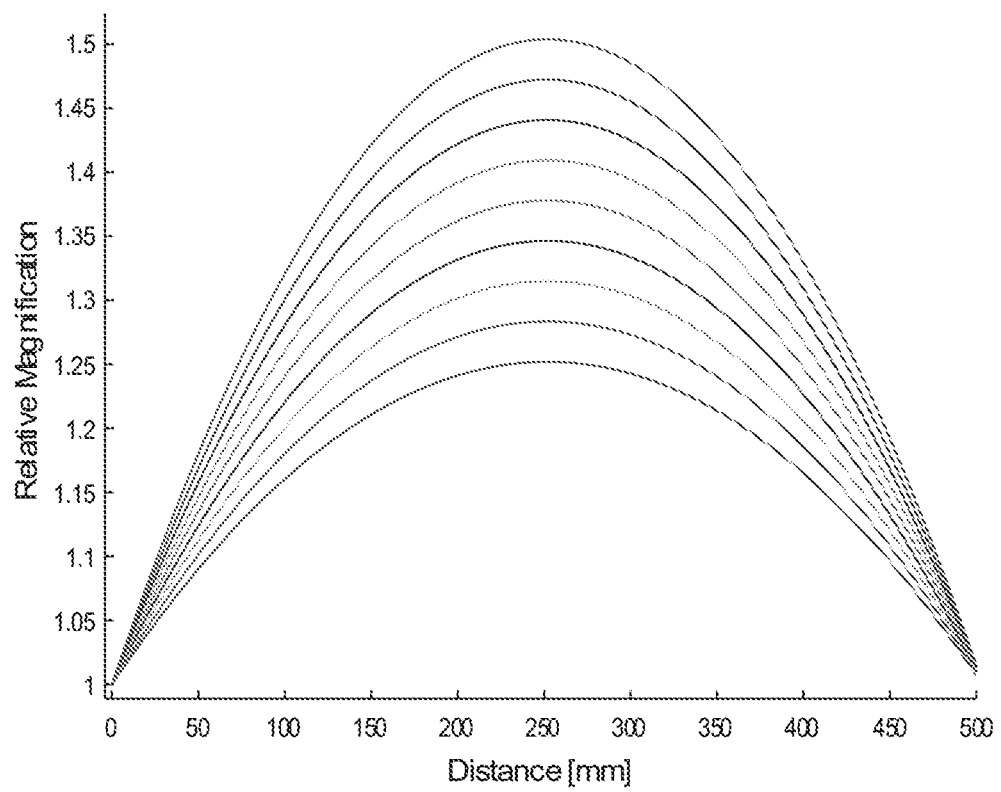

In some demonstrative embodiments, the plurality of magnification curves of FIG. 4D may correspond to a plurality of lenses having a lens power of between −2 D and −4 D, at 0.25 diopter intervals.

In other embodiments, any other curves may be used with respect to any other diopter ranges and/or any other diopter intervals.

In one example, a lens may have a lens power of −4 diopters. According to this example, it may be expected that the lens may have a maximal relative magnification of 1.5.

In another example, a lens may have a lens power of −4 D with a cylinder power of +0.25 D. According to this example, it may be expected that the lens may have a maximal relative magnification of 1.5 at a first axis, and a relative magnification of 1.47 at a second axis.

As shown in FIGS. 4A, 4B, and 4C and 4D, a change of few percent in magnification may be expected for a lens of 0.25 diopter.

In one example, a centimeter size object on the display 230 (FIG. 3) may occupy a few hundreds of pixels on the camera sensor. Accordingly, a change of a few percent in a size of the object may result in a change of a few pixels, which may be traceable.

Referring back to FIG. 1, in some demonstrative embodiments, one or more procedures, operations, and/or methods may be performed to measure the one or more optical parameters of the lens, e.g., as described below.

In some demonstrative embodiments, the one or more operations may include placing the lens of the eyeglasses between camera 118 and display 180.

In some demonstrative embodiments, parameters as a lens power, a lens cylindrical power, a lens cylinder angle, and/or any other parameters of the eyeglasses lens may be determined, for example, by tracking the change of the image captured by camera 118 via the lens.

In some demonstrative embodiments, determining the one or more optical parameters of the lens may be based for example, on the camera distance, e.g., between the object, which is displayed on display 130, and camera 118; the lens distance, e.g., between the object and the lens; and/or a detected change in the image, e.g., as described below.

In some demonstrative embodiments, application 160 may utilize the one or more operations to determine the one or more optical parameters of the lens, for example, based on a magnification between an imaged dimension of the object and a respective reference dimension of the object, which may be displayed on display 130, e.g., as described below.

In some demonstrative embodiments, application 160 may be configured to determine a spherical power of the lens based on the magnification, e.g., as described below.

In some demonstrative embodiments, application 160 may be configured to determine a cylindrical axis of the lens, for example, based on a maximal magnification axis of a plurality of axes in the image, at which a magnification between the imaged dimension and the reference dimension is maximal, e.g., as described below.

In some demonstrative embodiments, application 160 may be configured to determine the cylindrical power of the lens, for example, based on the maximal magnification axis, and a minimal magnification axis of the plurality of axes in the image, at which a magnification between another imaged dimension and another respective reference dimension of the object is minimal, e.g., as described below.

In some demonstrative embodiments, application 160 may be configured to determine the cylindrical power of the lens, for example, based on a first magnification at the minimal magnification axis, and a second magnification at the maximal magnification axis, e.g., as described below.

In some demonstrative embodiments, application 160 may be configured to determine the one or more optical parameters of the lens, for example, based on an extremum magnification image, e.g., a maximal or minimal magnification image, which may be selected from a plurality of magnification images, e.g., as described below.

In some demonstrative embodiments, the extremum magnification image of the plurality of images, may include an image in which a magnification between the imaged dimension and the reference dimension is maximal or minimal.

In some demonstrative embodiments, application 160 may be configured to process a plurality of images of the object captured via the lens at a respective plurality of camera distances, e.g., between the camera and the object, while the lens distance is constant. For example, application 160 may be configured to instruct the user of the eyeglasses to move camera 118 backward and/or forward from display 130, while the eyeglasses remain static with respect to display 130.

In some demonstrative embodiments, application 160 may be configured to determine an extremum magnification image of the plurality of images, which may have an extremum magnification between the imaged dimension and the reference dimension.

In some demonstrative embodiments, application 160 may be configured to determine the one or more optical parameters of the lens, for example, based on the extremum magnification image, e.g., as described below.

In some demonstrative embodiments, application 160 may be configured to process a plurality of images of the object captured via the lens at a respective plurality of lens distances, e.g., between the lens and the object, while the camera distance is constant. For example, application 160 may be configured to instruct the user eyeglasses to move the eyeglasses backward and/or forward between camera 118 and display 130, while the camera 118 remains static with respect to display 130.

In some demonstrative embodiments, application 160 may be configured to determine an extremum magnification image of the plurality of images, which provides n extremum of the magnification between the imaged dimension and the reference dimension.

In some demonstrative embodiments, application 160 may be configured to determine the one or more optical parameters of the lens, for example, based on the extremum magnification image, e.g., as described below.

In some demonstrative embodiments, application 160 may be configured to determine the one or more optical parameters of the lens, for example, based on the magnification, and another magnification of at least one dimension in an image of a calibration object having known dimensions, e.g., calibration object 301 (FIG. 3).

In some demonstrative embodiments, the image of the calibration object may be captured not via the lens, e.g., as described above with reference to FIG. 3.

In some demonstrative embodiments, application 160 may be configured to determine the first distance, e.g., between the object and camera 118, and/or the second distance, e.g., between the object and the lens, based on one or more distance measurements, estimations, and/or calculations, e.g., as described below.

In some demonstrative embodiments, the first distance and/or the second distance may be predefined, e.g., as described below.

In some demonstrative embodiments, the second distance may be set to include a distance between the object and the lens when temple arms of the eyeglasses are extended to a plane of the object.

In some demonstrative embodiments, application 160 may be configured to determine the first distance and/or the second distance, for example, based on acceleration information corresponding to an acceleration of camera 118 and/or device 102, e.g., when one or more images are captured by camera 118.

In some demonstrative embodiments, device 102 may include an accelerometer 126 configured to provide to application 160 the acceleration information of camera 118 and/or device 102.

In some demonstrative embodiments, application 160 may be configured to determine the first distance and/or the second distance, for example, based on one or more three-dimensional (3D) coordinates of the object.

In some demonstrative embodiments, device 102 may include a 3D sensor configured to determine one or more three-dimensional (3D) coordinates of an object.

In some demonstrative embodiments, application 160 may be configured to determine the first distance, for example, based on the object and at least one dimension in the image of a calibration object having known dimensions, e.g., calibration object 301 (FIG. 3).

In some demonstrative embodiments, application 160 may be configured to determine the one or more optical parameters of the lens, for example, according to one or more operations, e.g., as described below.

Figure 5:
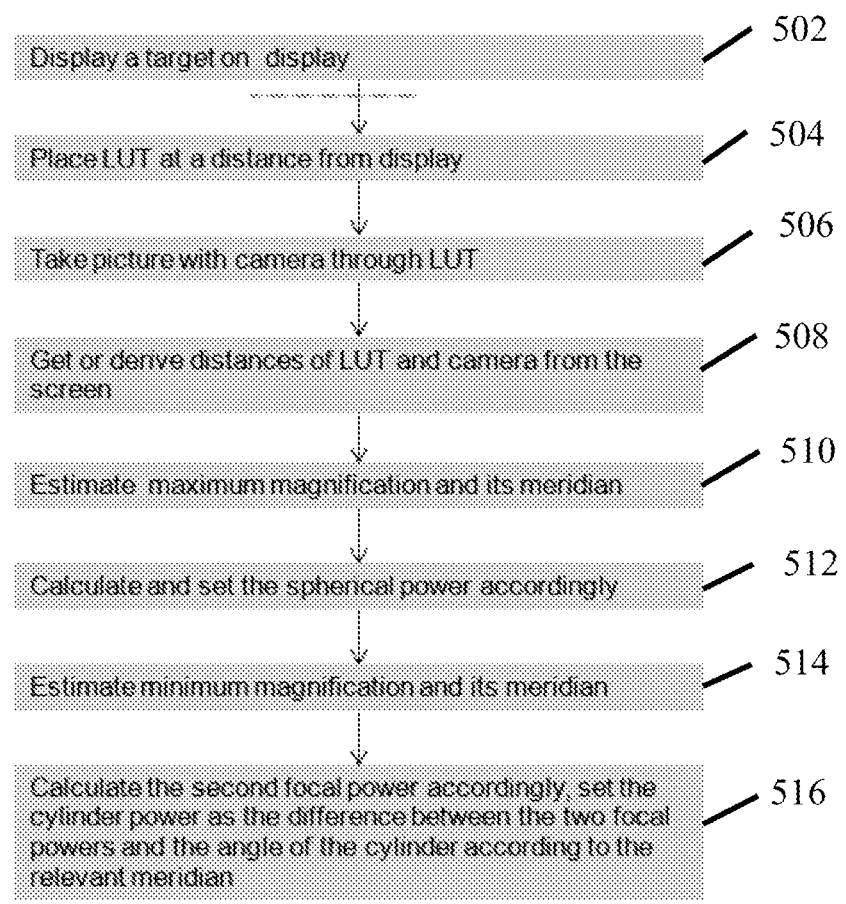
FIG. 5 is a schematic illustration of a method of determining one or more optical parameters of a lens, in accordance with some demonstrative embodiments.

Reference is made to FIG. 5, which schematically illustrates a method of determining one or more optical parameters of a lens, in accordance with some demonstrative embodiments. For example, one or operations of the method of FIG. 5 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 502, the method may include displaying an object on a display. For example, application 160 (FIG. 1) may cause display 130 (FIG. 1) to display the object, e.g., as described above.

As indicated at block 504, the method may include placing an eyeglasses lens (also referred to as "Lens Under Test (LUT)") at a certain distance from the display. For example, application 160 (FIG. 1) may instruct the user to place the lens at the lens distance from the display 130 (FIG. 1), e.g., as described above.

As indicated at block 506, the method may include capturing with a camera through the eyeglasses lens an image of the object displayed on the display. For example, application 160 (FIG. 1) may cause camera 118 (FIG. 1) to capture the image of the object, for example, via the lens, e.g., as described above.

As indicated at block 508, the method may include determining a first distance of the camera from the display, e.g., the camera distance, and a second distance of the eyeglasses lens from the display, e.g., the lens distance. For example, application 160 (FIG. 1) may determine the lens distance and the camera distance, e.g., as described above.

In some demonstrative embodiments, the camera distance and/or the lens distance may be estimated, given and/or advised to the user.

As indicated at block 510, the method may include estimating a maximal magnification of the object for a certain meridian, e.g., as described below with respect to an exemplary object. For example, application 160 (FIG. 1)

may estimate a magnification of the object for the certain meridian, e.g., as described above.

As indicated at block 512, the method may include calculating a focal power of the lens for the certain meridian. For example, application 160 (FIG. 1) may determine a focal power of the eyeglasses lens for the corresponding axis, e.g., as described above.

As indicated at block 514, if the magnification varies for various meridians, the method may include, locating the minimum magnification and a corresponding meridian and calculating its focal power. For example, application 160 (FIG. 1) may determine that the magnification varies for a few meridians and, accordingly application 160 (FIG. 1) may the minimal magnification axis and the magnification of the minimal magnification axis, e.g., as described below.

As indicated at block 516, the method may include determining the cylindrical power as the difference between the two focal powers and the angle of the cylinder. For example, application 160 (FIG. 1) may determine the cylindrical power of the lens, for example, based on the first magnification at the minimal magnification axis, and the second magnification at the maximal magnification axis, e.g., as described below.

In some demonstrative embodiments, application 160 (FIG. 1) may be configured implement one or more techniques to perform the operation of block 508, e.g., to determine the camera distance and/or the lens distance.

In some demonstrative embodiments, application 160 (FIG. 1) may be configured to perform one or more operations to determine the camera distance and/or the lens distance, e.g., as described below.

In some demonstrative embodiments, determining the camera distance and/or the lens distance may include displaying a calibration object having a known size on the display, capturing an image of the display with the camera, and evaluating the distance based on the captured image of the calibration object.

In some demonstrative embodiments, determining the camera distance and/or the lens distance may include measuring the distance from the camera to the display with a reference known size object, e.g., such as a Letter, an A4 paper, a meter, and/or the like.

In some demonstrative embodiments, determining the camera distance and/or the lens distance may include measuring the displacement of the camera from the display, for example, by integrating accelerometer data, e.g., from the accelerometer 126 (FIG. 1).

In some demonstrative embodiments, determining the camera distance and/or the lens distance may include using a 3D sensor or a depth camera, for example, to determine the camera distance and/or the lens distance.

Referring back to FIG. 1, in some demonstrative embodiments, application 160 (FIG. 1) may be configured to determine the optical parameters of the lens based on one or measurement schemes, e.g., as described below.

In some demonstrative embodiments, a first measurement scheme may include placing the lens at the middle between the camera 118 and the display 130, for example, such that the lens distance is approximately half of the camera distance, e.g., as described below.

In some demonstrative embodiments, a second measurement scheme may include placing the eyeglasses with temple arms extended against the display 130, for example, to locate the eyeglasses at a predefined rough distance, for example, such that the lens distance is based on the length of the arm temples, for example, about 14.5 cm, e.g., as described below.

In some demonstrative embodiments, a third measurement scheme may include keeping the camera 118 at a relatively fixed distance from the display 130 and capturing images through the lens, while moving the lens from the camera 118 towards the display 130 and/or backwards from display 130 to the camera 118.

In some demonstrative embodiments, the lens distance may be determined to be approximately half of the camera distance, for example, at a location, at which an image captured via the lens has a maximum relative magnification, e.g., as described below.

In some demonstrative embodiments, a fourth measurement scheme may include placing the eyeglasses lens at a certain distance from the display, and capturing a few images by the camera while changing the camera position, for example, to determine the location, at which an image captured via the lens has maximum relative magnification, e.g., as described below.

In some demonstrative embodiments, a fifth measurement scheme may include placing the frame of the eyeglasses at a certain distance from the display, capturing an image through the lens where the camera is located at a distance from the lens, and determining the lens distance from a size of the frame of the eyeglasses in an image captured by the camera, e.g., as described below.

In some demonstrative embodiments, a sixth measurement scheme may include placing the eyeglasses at a known distance from the display, for example, by extending the temple arms, or by using any other method to determine a known distance, and placing the camera at another known distance to capture an image through the lens.

In some demonstrative embodiments, according to the sixth measurement scheme the lens distance may be known, and the camera distance may be calculated, for example, based on a known size image displayed on the display 130 and the camera parameters, e.g., as described below.

In some demonstrative embodiments, application 160 may be configured to perform one or more operations to estimate the camera distance, the lens distance and/or the one or more optical parameters of the lens, for example, according to the first measurement scheme, e.g., as described below.

Figure 6:
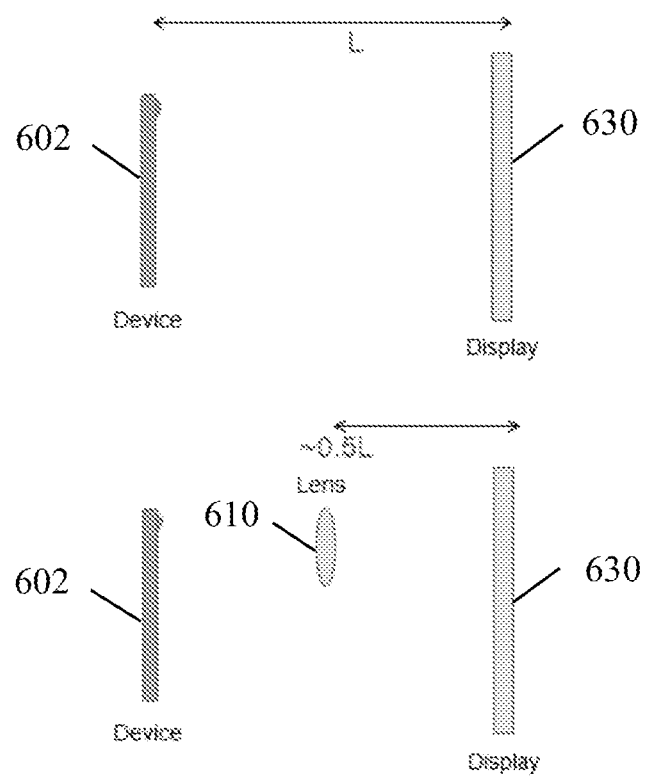
FIG. 6 is a schematic illustration of a measurement scheme, in accordance with some demonstrative embodiments.

Reference is made to FIG. 6, which schematically illustrates a measurement scheme 600, in accordance with some demonstrative embodiments. For example, one or operations using the measurement scheme 600 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, measurement scheme 600 may be configured to enable to determine one or more optical parameters of a lens 610, for example, according to the first measurement scheme.

In some demonstrative embodiments, as shown in FIG. 6, an image capturing device 602, may be placed at a known distance, denoted L, e.g., the camera distance, from a display 630. For example, device 602 may perform the functionality of camera 118 (FIG. 1); and/or display 630 may perform the functionality of display 130 (FIG. 1).

In some demonstrative embodiments, the camera distance L may be verified by the user and/or may be calculated based on an image of a calibration object, and one or more parameters of the camera, e.g., a focal length, a field of view, and/or a sensor pitch.

In some demonstrative embodiments, as shown in FIG. 6, the lens may be placed approximately midway between the device 602 and the display 630, e.g., at a distance, denoted 0.5 L.

In some demonstrative embodiments, since a sensitivity to the positioning of the lens at the center is low, accurate estimation of the one or more optical parameters of the lens may be achieved. Positioning the lens, e.g., even within few centimeters from the middle between the camera and the display, may still enable to determine the one or more optical parameters of the lens as if the lens was positioned exactly in the middle between the camera and the display.

Figure 7:
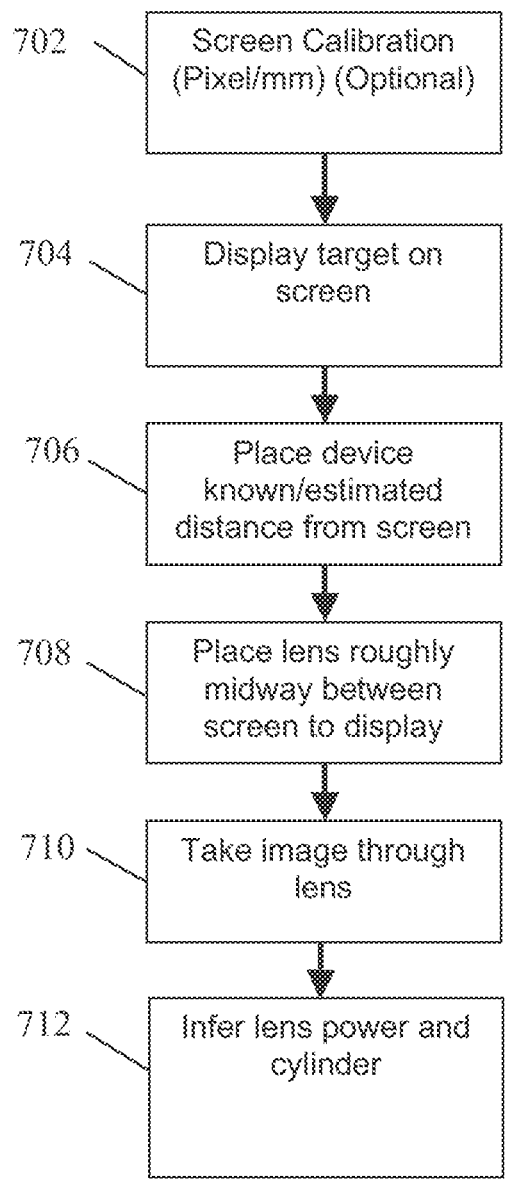
FIG. 7 is a schematic flow-chart illustration of a method of determining one or more optical parameters of a lens, in accordance with some demonstrative embodiments.

Reference is made to FIG. 7, which schematically illustrates a method of determining one or more optical parameters of a lens, in accordance with some demonstrative embodiments. For example, one or operations of the method of FIG. 7 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, one or more operations of the method of FIG. 7 may be performed, for example, using the first measurement scheme, e.g., measurement scheme 600 (FIG. 6).

As indicated at block 704, the method may include displaying an object on a display. For example, application 160 (FIG. 1) may cause display 130 (FIG. 1) to display the object, e.g., as described above.

As indicated at block 702, the method may optionally include calibrating the display, e.g., as described below.

As indicated at block 706, the method may include placing a camera device at a known or estimated distance from the display. For example, application 160 (FIG. 1) may instruct the user to place camera 118 (FIG. 1) at a certain distance from the display 130 (FIG. 1), e.g., as described above with reference to FIG. 6.

As indicated at block 708, the method may include placing a lens roughly midway between the display and camera. For example, application 160 (FIG. 1) may instruct the user to place the lens at the middle between camera 118 (FIG. 1) and display 130 (FIG. 1), e.g., as described above with reference to FIG. 6.

As indicated at block 710, the method may include capturing an image of the displayed image through the lens. For example, application 160 (FIG. 1) may cause camera 118 (FIG. 1) to capture the image of the object, for example, via the lens, e.g., as described above.

As indicated at block 712, the method may include analyzing the captured image, and determining the power and cylinder of the lens. For example, application 160 (FIG. 1) may determine the one or more optical parameters of the lens, for example, based on the captured image, e.g., as described above.

Referring back to FIG. 1, in some demonstrative embodiments, application 160 may be configured to perform one or more operations to estimate the camera distance, the lens distance and/or the one or more optical parameters of the lens, for example, according to the second measurement scheme, e.g., as described below.

Figure 8:
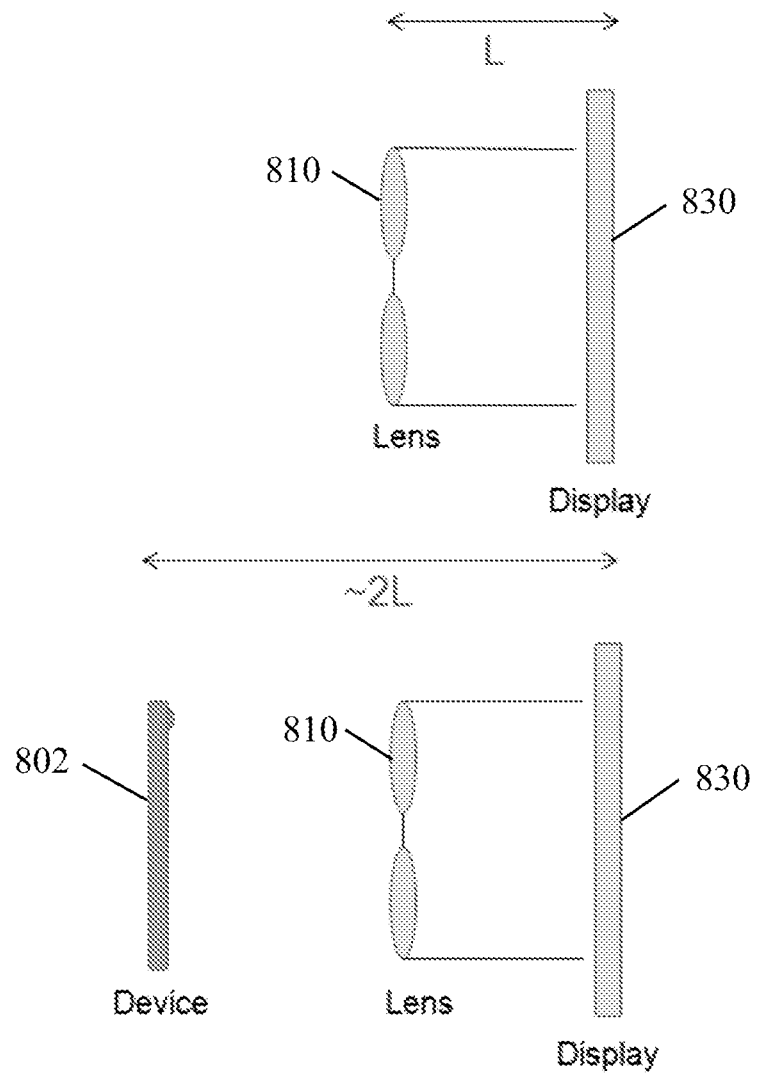
FIG. 8 is a schematic illustration of a measurement scheme, in accordance with some demonstrative embodiments.

Reference is made to FIG. 8, which schematically illustrates a measurement scheme 800, in accordance with some demonstrative embodiments. For example, one or operations of using the measurement scheme 800 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, measurement scheme 800 may be configured to enable to determine one or more optical parameters of a lens 810, for example, according to the second measurement scheme.

In some demonstrative embodiments, as shown in FIG. 8, a lens 810 may be placed at a known distance, denoted L, from a display 830. For example, display 830 may perform the functionality of display 130 (FIG. 1).

In some demonstrative embodiments, as shown in FIG. 7, lens 810 may be placed at the distance L by completely extending the temple arms of the eyeglasses and allowing them to touch the display 830.

In some demonstrative embodiments, since the temple arm is of fixed length, e.g., of typically 13.5 cm to 15 cm, the distance between the lens and the display may be well defined.

In some demonstrative embodiments, as shown in FIG. 8, an image capturing device 802, may be placed at a distance, denoted 2 L, from display 830, e.g., a distance approximately equal to twice the length of the temple arm. For example, device 802 may perform the functionality of camera 118 (FIG. 1).

In some demonstrative embodiments, the one or more optical parameters of the lens may be determined, for example, by capturing an image of the object from the distance 2 L.

Figure 9:
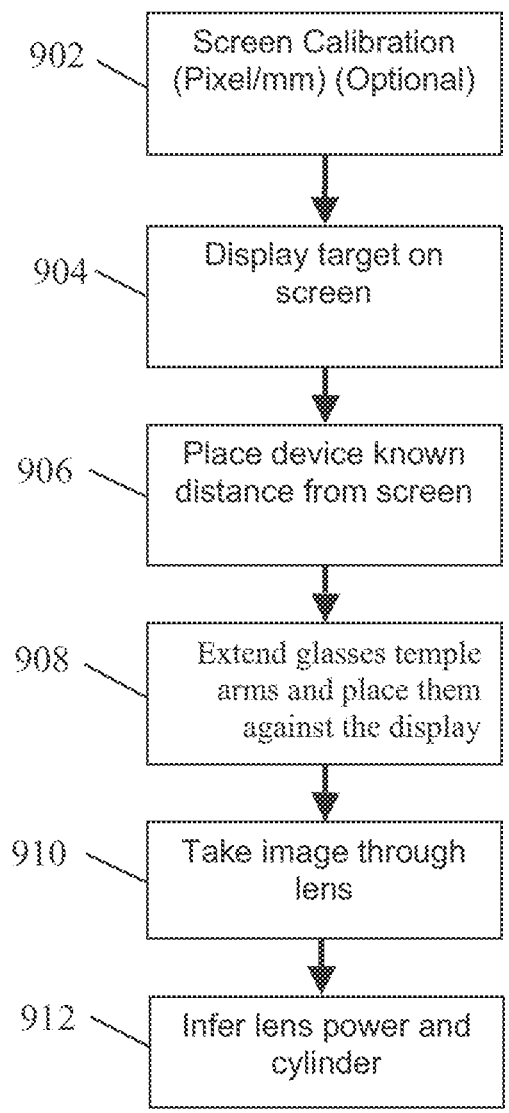
FIG. 9 is a schematic flow-chart illustration of a method of determining one or more optical parameters of a lens, in accordance with some demonstrative embodiments.

Reference is made to FIG. 9, which schematically illustrates a method of determining one or more optical parameters of a lens, in accordance with some demonstrative embodiments. For example, one or operations of the method of FIG. 9 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, one or more operations of the method of FIG. 9 may be performed, for example, in accordance with the second measurement scheme, e.g., measurement scheme 800 (FIG. 8).

As indicated at block 902, the method may optionally include calibrating a screen to find a pixel/mm ratio. For example, application 160 (FIG. 1) may be configured to calibrate display 130 (FIG. 1), e.g., as described below.

As indicated at block 904, the method may include extending the eyeglasses temple arms and placing them against the display. For example, application 160 (FIG. 1) may instruct the user to extend the eyeglasses temple arms and to place them against the display 130 (FIG. 1), e.g., as described above.

As indicated at block 906, the method may include placing a camera device at a known or estimated distance from the display, e.g., approximately twice the length of the temple arm. For example, application 160 (FIG. 1) may instruct the user to place camera 118 (FIG. 1) at a known or estimated distance from display 130 (FIG. 1), e.g., as described above.

As indicated at block 908, the method may include capturing an image through lens. For example, application 160 (FIG. 1) may cause camera 118 (FIG. 1) to capture the image of the object, for example, via the lens, e.g., as described above.

As indicated at block 910, the method may include determining lens power and cylinder power and cylinder axis. For example, application 160 (FIG. 1) may determine the one or more optical parameters of the lens, for example, based on the captured image, e.g., as described above.

Referring back to FIG. 1, in some demonstrative embodiments, application 160 may be configured to perform one or more operations to estimate the camera distance, the lens distance and/or the one or more optical parameters of the lens, for example, according to the third measurement scheme, e.g., as described below.

Figure 10:
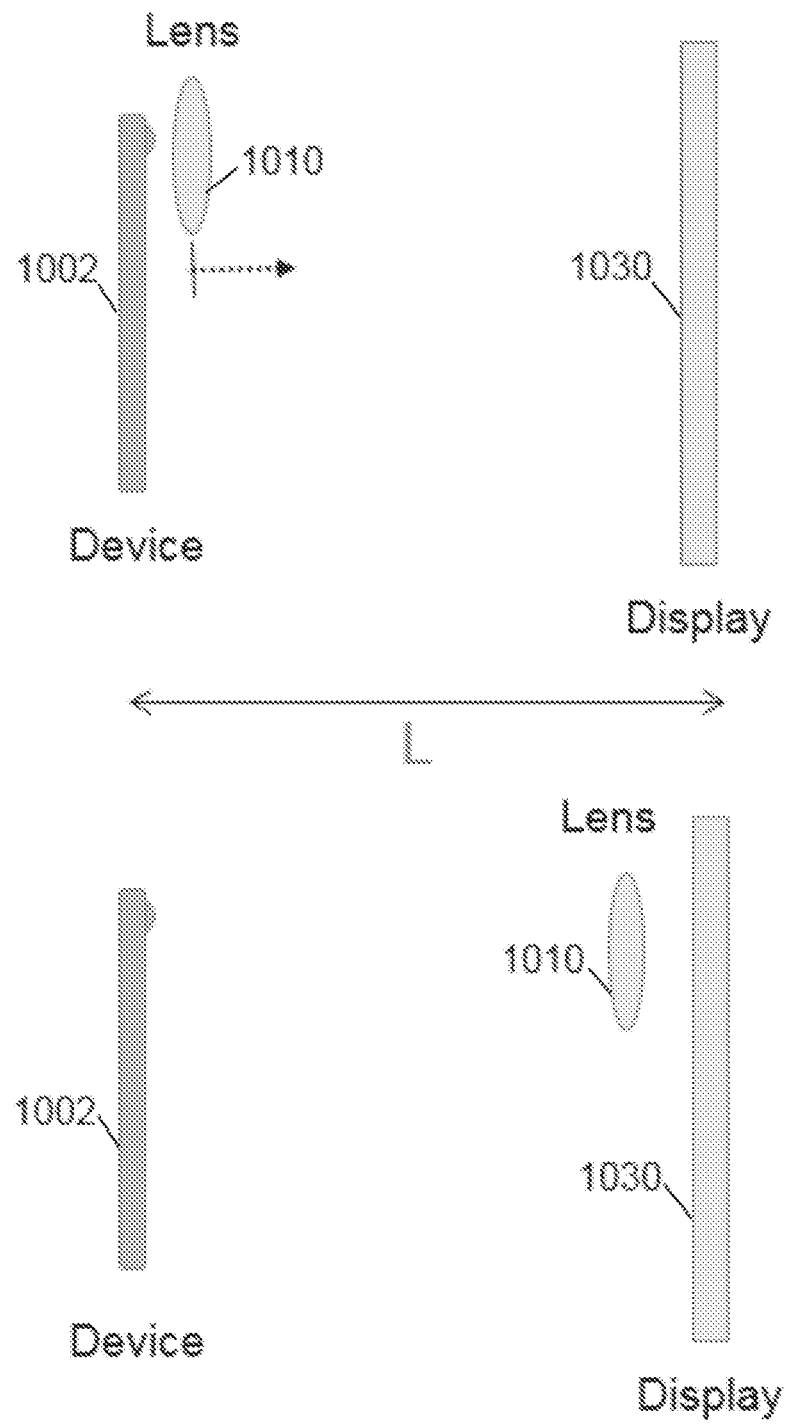
FIG. 10 is a schematic illustration of a measurement scheme, in accordance with some demonstrative embodiments.

Reference is made to FIG. 10, which schematically illustrates a measurement scheme 1100, in accordance with some demonstrative embodiments. For example, one or operations using of the measurement scheme 1000 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, measurement scheme 1000 may be configured to enable to determine one or more optical parameters of a lens 1010, for example, according to the third measurement scheme.

In some demonstrative embodiments, as shown in FIG. 10, an image capturing device 1002, may be placed at a certain distance, denoted L, e.g., the camera distance, from a display 1030. For example, device 1002 may perform the functionality of camera 118 (FIG. 1); and/or display 1030 may perform the functionality of display 130 (FIG. 1).

In some demonstrative embodiments, as shown in FIG. 10, the lens 1010 may be moved between the device 1002 and the display 1030, for example, in order to find the maximal relative magnification.

In some demonstrative embodiments, according to measurement scheme 1000 the position of the lens may not need to be monitored.

Figure 11:
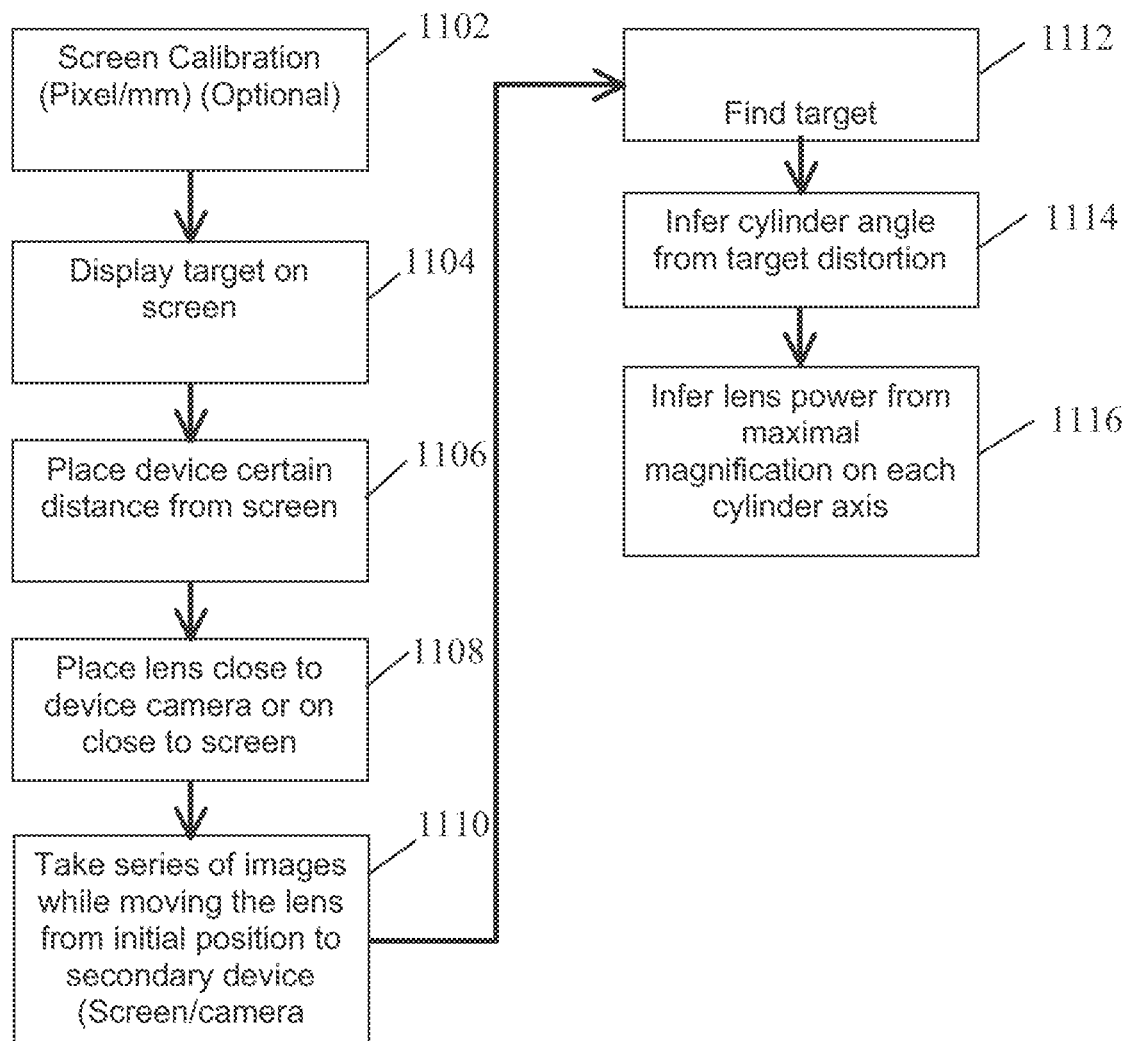
FIG. 11 is a schematic flow-chart illustration of a method of determining one or more optical parameters of a lens, in accordance with some demonstrative embodiments.

Reference is made to FIG. 11, which schematically illustrates a method of determining one or more optical parameters of a lens, in accordance with some demonstrative embodiments. For example, one or operations of the method of FIG. 11 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, one or more operations of the method of FIG. 11 may be performed, for example, in accordance with the third measurement scheme, e.g., measurement scheme 1000 (FIG. 11).

As indicated at block 1102, the method may optionally include calibrating a screen to find a pixel/mm ratio. For example, application 160 (FIG. 1) may be configured to calibrate display 130 (FIG. 1), e.g., as described below.

As indicated at block 1104, the method may include displaying an object on the display. For example, application 160 (FIG. 1) may cause display 130 (FIG. 1) to display the object, e.g., as described above.

As indicated at block 1106, the method may include holding a camera device at a certain distance from the display. For example, application 160 (FIG. 1) may instruct the user to place camera 118 (FIG. 1) at a certain distance from the display 130 (FIG. 1), e.g., as described above.

In some demonstrative embodiments, the method may include calculating the camera distance. For example, application 160 (FIG. 1) may determine the camera distance, e.g., as described above.

As indicated at block 1108, the method may include placing a lens close to the camera 118. For example, application 160 (FIG. 1) may instruct the user to place the lens close to camera 118 (FIG. 1), e.g., as described above.

As indicated at block 1110, the method may include capturing a series of images while moving the lens towards the display. For example, application 160 (FIG. 1) may cause camera 118 (FIG. 1) to capture a series of images while moving the lens towards the display 130 (FIG. 1), e.g., as described above.

In other embodiments, the lens may be moved away from the display and towards the camera. For example, the lens may be placed close to the display, and a series of images may be captured while moving the lens towards the camera.

In some demonstrative embodiments, a first option or a second option may be used to determine when to stop the moving of the lens towards the display.

In some demonstrative embodiments, the first option may include stopping when the lens is very close to the display.

In some demonstrative embodiments, the second option may include calculating a relative magnification for an arbitrary axis, and stopping the movement after the magnification reaches its peak.

As indicated at block 1112, the method may include determining the image with the maximal magnification, and checking for cylindrical distortion. For example, application 160 (FIG. 1) may determine the cylindrical axis, for example, based on the maximal magnification of the object for the certain meridian, e.g., as described below.

In one example, when a circular object is used, an ellipse shape may be seen.

As indicated at block 1116, the method may include calculating the lens power and the cylindrical power, based on the relative magnification in each axes and the distance. For example, application 160 (FIG. 1) may determine the focal power and the cylindrical power of the eyeglasses lens, for example, based on the magnifications in each axes, e.g., as described above.

In some demonstrative embodiments, the method may optionally include checking for consistency of the cylindrical distortion at the rest of the captured images.

In one example, the consistency of the cylindrical distortion may indicate an unintended rotation during movement.

Referring back to FIG. 1, in some demonstrative embodiments, application 160 may be configured to perform one or more operations to estimate the camera distance, the lens distance and/or the one or more optical parameters of the lens, for example, according to the fourth measurement scheme, e.g., as described below.

Figure 12:
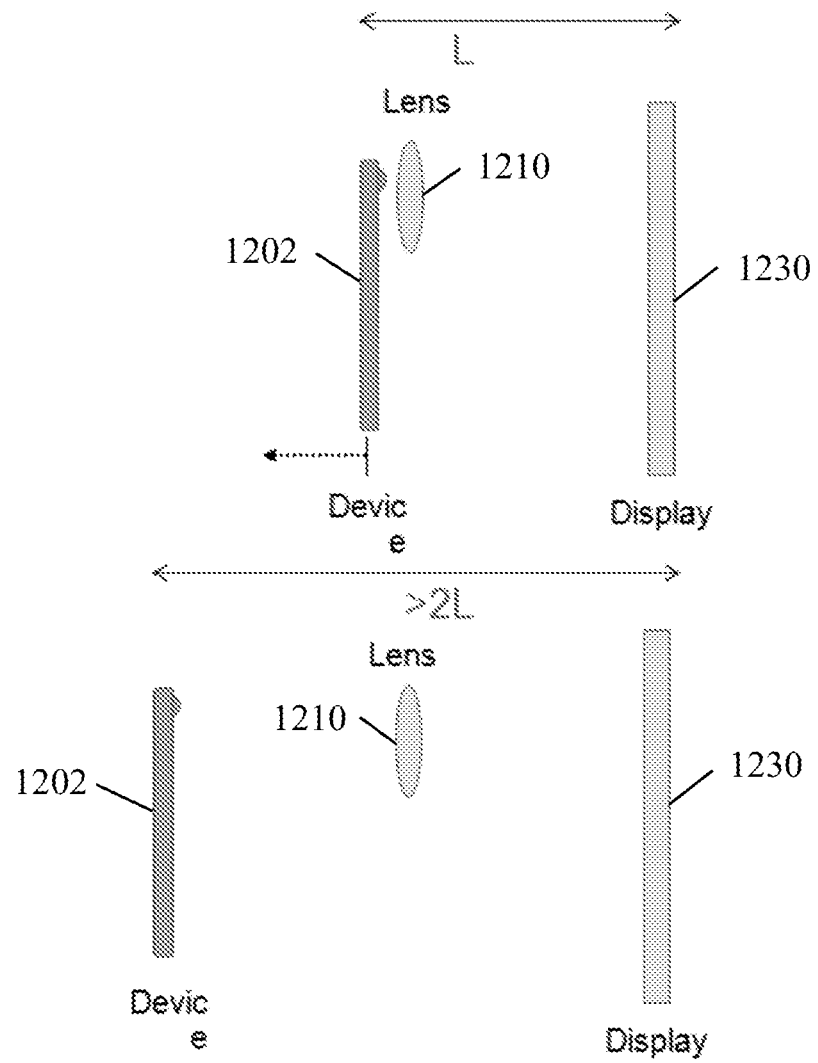
FIG. 12 is a schematic illustration of a measurement scheme, in accordance with some demonstrative embodiments.

Reference is made to FIG. 12, which schematically illustrates a measurement scheme 1200, in accordance with some demonstrative embodiments. For example, one or operations using of the measurement scheme 1200 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, measurement scheme 1200 may be configured to determine one or more optical parameters of a lens 1210, for example, according to the fourth measurement scheme.

In some demonstrative embodiments, as shown in FIG. 12, the lens may be placed at a certain distance, denoted L, e.g., the lens distance, from a display 1230. For example, or display 1230 may perform the functionality of display 130 (FIG. 1).

In some demonstrative embodiments, as shown in FIG. 2, an image capturing device 1202 may be placed close to lens 1210. For example, device 1002 may perform the functionality of camera 118 (FIG. 1).

In some demonstrative embodiments, as shown in FIG. 12, the device 1202 may be moved away from lens 1210 up to a distance, denoted 2 L, e.g., the camera distance, for example, in order to find the maximal relative magnification.

In other embodiments, the device 1202 may be placed at approximately the distance 2 L from the display and moved towards lens 1210, e.g., while capturing a series of images of the displayed object via the lens 1210.

In some demonstrative embodiments, if several images are captured, a selected image, e.g., the image with maximal relative magnification, may be used to determine one or more of, e.g., all, the optical parameters of lens 1210, for example, by determining the camera distance, for example, from a known size object captured at the selected image, and determining the lens distance as half of the camera-display distance.

Figure 13:
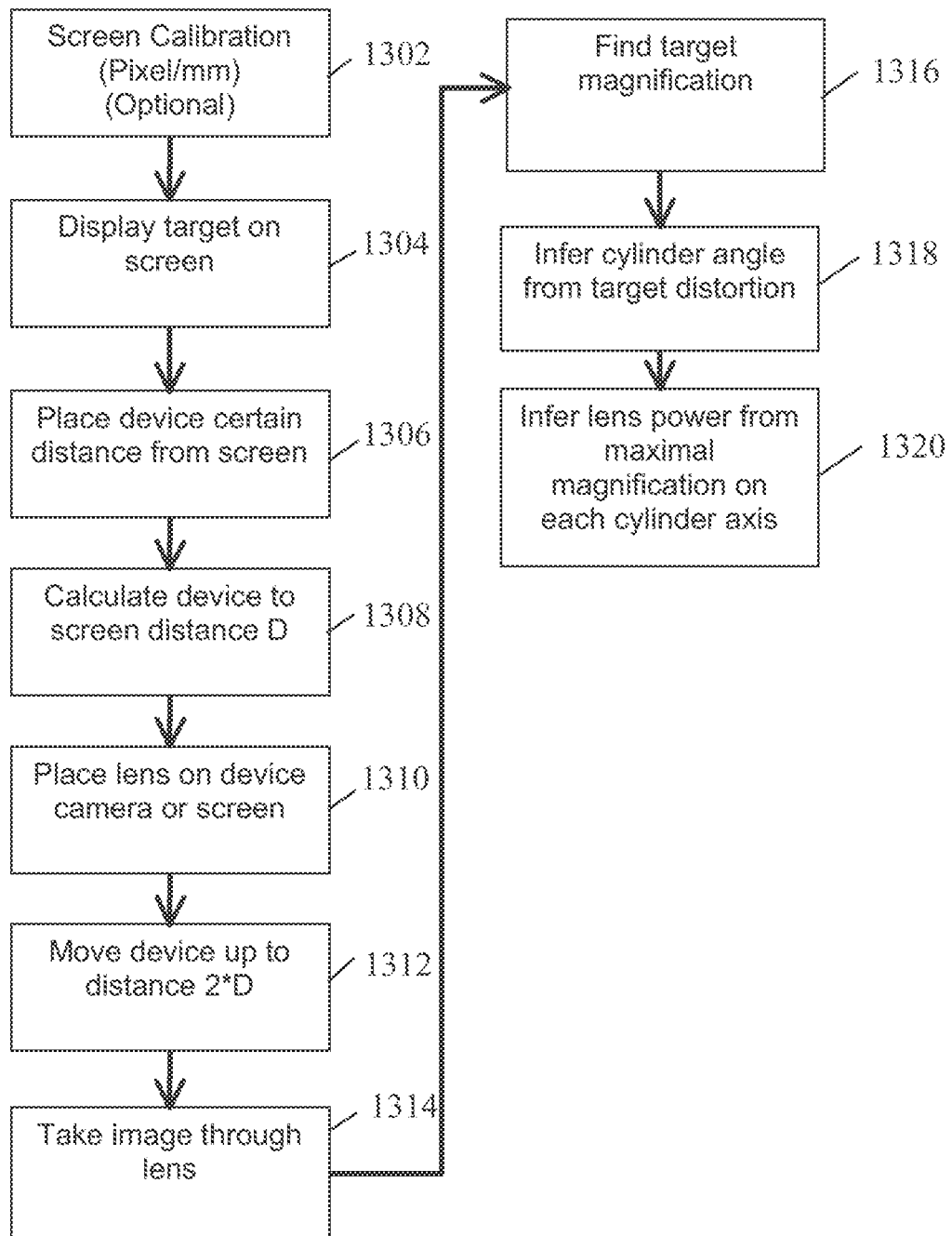
FIG. 13 is a schematic flow-chart illustration of a method of determining one or more optical parameters of a lens, in accordance with some demonstrative embodiments.

Reference is made to FIG. 13, which schematically illustrates a method of determining one or more optical parameters of a lens, in accordance with some demonstrative embodiments. For example, one or operations of the method of FIG. 13 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, one or more operations of the method of FIG. 13 may be performed, for example, in accordance with the fourth measurement scheme, e.g., measurement scheme 1200 (FIG. 12).

As indicated at block 1302, the method may optionally include calibrating a screen to find a pixel/mm relationship. For example, application 160 (FIG. 1) may be configured to calibrate display 130 (FIG. 1), e.g., as described below.

As indicated at block 1304, method may include displaying an object on the display. For example, application 160 (FIG. 1) may cause display 130 (FIG. 1) to display the object, e.g., as described above.

As indicated at block 1306, the method may include holding camera 118 at a certain distance from the display. For example, application 160 (FIG. 1) may instruct the user to place camera 118 (FIG. 1) at a certain distance, denoted D, from the display 130 (FIG. 1), e.g., as described above.

As indicated at block 1308, the method may include calculating the camera distance. For example, application 160 (FIG. 1) may determine the camera distance, e.g., as described above.

As indicated at block 1310, the method may include placing the lens at the same distance as the device. For example, application 160 (FIG. 1) may instruct the user to place the lens close to camera 118 (FIG. 1), e.g., as described above.

As indicated at block 1312, the method may include moving camera 118 backwards up to a distance 2 D. For example, application 160 (FIG. 1) may instruct the user to move camera 118 (FIG. 1) to the distance 2 D, e.g., as described above.

As indicated at block 1314, the method may include capturing an image of the object through the lens. For example, application 160 (FIG. 1) may cause camera 118 (FIG. 1) to capture an image via the lens, e.g., as described above.

As indicated at block 1316, the method may include determining the image with the maximal magnification, and checking for cylindrical distortion at the object. For example, application 160 (FIG. 1) may determine the maximal magnification of the object for the certain meridian, e.g., as described above.

In one example, for a circular object an ellipse shape may be seen, e.g., as described below.

As indicated at block 1318, the method may include determining a cylinder angle from the image distortion. For example, application 160 (FIG. 1) may determine the cylindrical axis, for example, based on the maximal magnification of the object for the certain meridian, e.g., as described above.

As indicated at block 1320, the method may include, e.g., for each of the axes, determining the relative magnification, and calculating lens power. For example, application 160 (FIG. 1) may determine the focal power and the cylindrical power of the eyeglasses lens, for example, based on the magnifications in each axes, e.g., as described above.

Referring back to FIG. 1, in some demonstrative embodiments, application 160 may be configured to perform one or more operations to estimate the camera distance, the lens distance and/or the one or more optical parameters of the lens, for example, according to the fifth measurement scheme, e.g., as described below.

Figure 14:
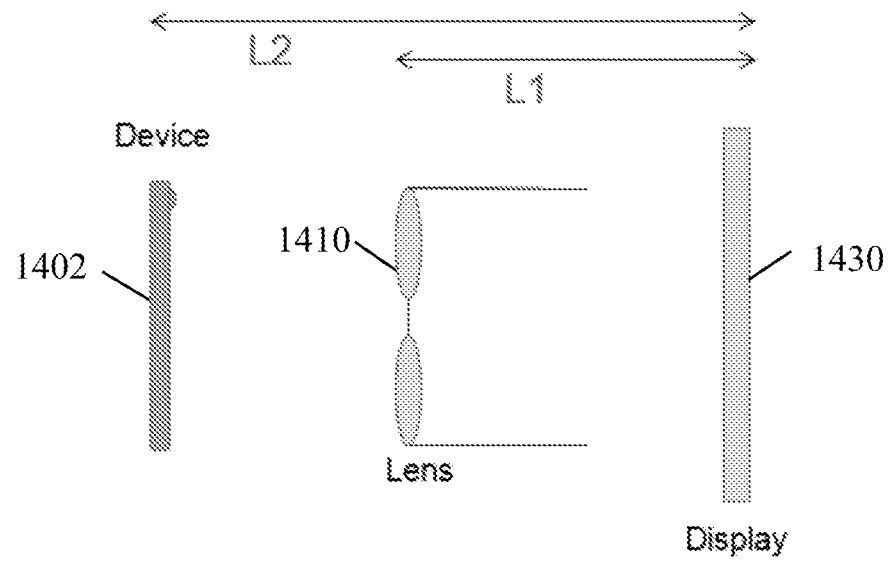
FIG. 14 is a schematic illustration of a measurement scheme, in accordance with some demonstrative embodiments.

Reference is made to FIG. 14, which schematically illustrates a measurement scheme 1400, in accordance with some demonstrative embodiments. For example, one or more operations using of the measurement scheme 1400 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, measurement scheme 1400 may be configured to determine one or more optical parameters of a lens 1410, for example, according to the fifth measurement scheme.

In some demonstrative embodiments, as shown in FIG. 14, an image capturing device 1402, may be placed at a certain distance, denoted L2, e.g., the camera distance, from a display 1430. For example, device 1402 may perform the functionality of camera 118 (FIG. 1); and/or display 1430 may perform the functionality of display 130 (FIG. 1).

In some demonstrative embodiments, as shown in FIG. 14, the lens 1420 may be placed at a distance, denoted L1, e.g., the lens distance, between lens 1420 and display 1430.

In some demonstrative embodiments, as shown in FIG. 14, the device 1402 may capture through the lens 1410 an image of an object displayed on display 1430.

In some demonstrative embodiments, the camera distance L2, and/or the lens distance L1 may be arbitrary.

In some demonstrative embodiments, an absolute feature of a frame including the lens 1410 or the frame distance from the display may be considered as known or calibrated.

In some demonstrative embodiments, for a known or calibrated frame size, or any other feature within the frame ("the calibration object"), the lens distance and the camera distance may be estimated, e.g., as described below.

In some demonstrative embodiments, the calibration object may have a height, denoted h, which may be known and/or given.

In some demonstrative embodiments, the known object height h may be considered as a known or calibrated feature of the frame, for example, the height of the lens, the width of the frame, the bridge length, and/or any other part of the eyeglasses.

In some demonstrative embodiments, a feature size of an element of the frame may also be given, for example, from a query to a database of a specified frame model, and/or may be specified by a user of device 102 (FIG. 1).

In some demonstrative embodiments, an image of the calibration object ("the calibration image"), e.g., when captured via the lens, may have an imaged height, denoted h'.

In some demonstrative embodiments, a distance, denoted u, between the lens and the calibration object may be determined, for example, based on the EFL of the lens, which may be known and/or given, the height h, and/or the imaged height h', e.g., as described below.

In some demonstrative embodiments, the following Equation may be given, for example, based on triangles similarity, e.g., as follows:

$$\frac{h'}{h} = \frac{v}{u} \cong \frac{efl}{u} \qquad (16)$$

wherein v is approximately the EFL of the lens.

In some demonstrative embodiments, the imaged height h' of the calibration image may be based on a number of pixels, denoted h'_pixels_estimated, occupied by the calibration image, and a sensor pitch, denoted pitch, of the lens, e.g., as follows:

$$h' = \text{pitch} * h'\_pixels\_estimated \qquad (17)$$

In some demonstrative embodiments, the distance u may be determined, for example, based on Equation 16 and Equation 17, e.g., as follows:

$$u \cong \frac{efl * h}{h'} = \frac{efl}{\text{pitch}} * \frac{h}{h'\_pixels\_estimated} \qquad (18)$$

Referring back to FIG. 1, in some demonstrative embodiments, application 160 may be configured to perform one or more operations to estimate the camera distance, the lens distance and/or the one or more optical parameters of the lens, for example, according to the sixth measurement scheme, e.g., as described below.

Figure 15:
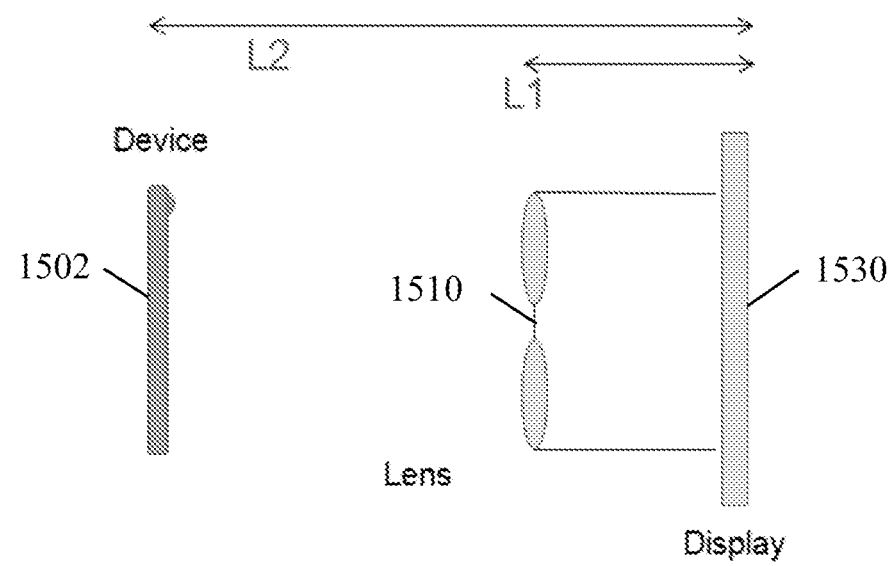
FIG. 15 is a schematic illustration of a measurement scheme, in accordance with some demonstrative embodiments.

Reference is made to FIG. 15, which schematically illustrates a measurement scheme 1500, in accordance with some demonstrative embodiments. For example, one or more operations using of the measurement scheme 1500 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, measurement scheme 1500 may be configured to determine one or more optical parameters of a lens 1510, for example, according to the sixth measurement scheme.

In some demonstrative embodiments, as shown in measurement scheme 1500, the lens 1510 may be placed at a distance, denoted L1, e.g., the lens distance, between lens 1510 and a display 1530. For example, display 1530 may perform the functionality of display 130 (FIG. 1).

In some demonstrative embodiments, the distance L1, of the frame from the display 1530 may be known.

In some demonstrative embodiments, the lens distance L1 may be known, for example, due to placing the frame at a predefined distance, placing the temple arms extended against the display, measuring the distance of the frame from the display and/or using any other method to determine the distance of the frame from the display or from the camera.

In some demonstrative embodiments, device 1502, may be located at any given distance, denoted L2, e.g., a predefined distance or an arbitrary distance, from the display 1530, e.g., the camera distance, for example, as long as device 1502 is able to capture an image of the object displayed on the display 1530, e.g., through the lens 1510.

In some demonstrative embodiments, the camera distance L2, between the display and the device, may be calculated from an object having a known size that that may be displayed on display 1530, for example, and one or more parameters of the camera 1502, e.g., a focal length, a field of view, and/or a sensor pitch, e.g., as described below.

Referring back to FIG. 1, in some demonstrative embodiments, device 102 may perform one or more operations, for example, to calibrate one or more elements of the frame, e.g., as described below.

In some demonstrative embodiments, the frame may be calibrated, for example, by placing the frame against the display 130 and capturing an image including the frame and the display 130, which may present a calibration object having known sizes.

In some demonstrative embodiments, an auto-detection or a manual detection of a feature of the frame may be scaled, for example, using the calibration object displayed upon the display 130.

In some demonstrative embodiments, the frame may be calibrated, for example, by placing the frame at a known distance from the display 130, e.g., as described below.

In some demonstrative embodiments, by extending the temple arms of the eyeglasses and placing them against the display 130, the distance of the frame surrounding the lenses from the display 130 may be regarded as about 145 mm.

In some demonstrative embodiments, a feature of the frame may be calibrated, for example, according to the magnification of the displayed image of the calibration object, e.g., for the distance of 145 mm, and one or more camera lens properties.

In some demonstrative embodiments, the frame can be calibrated, for example, using the fact that the maximum magnification occurs, for example, when the eyeglasses are just in the middle between the display 130 and camera 118.

In some demonstrative embodiments, using this fact it may be determined that the distance of an actual location of the frame is half a measured distance between the device 102 and the display 130.

In some demonstrative embodiments, using a known distance converted into an absolute magnification, where the focal length and sensor pixel pitch are given may be determined, e.g., as follows:

$$h = \frac{h'_{pixels} * \text{pitch} * (L - f)}{2f} \qquad (19)$$

wherein $h'_{pixels}$ is the amount of pixels that the frame feature is accommodating on the sensor, pitch is the distance from one pixel to an adjacent pixel, L is the distance between the display and the device and/or f is the focal length of the camera.

In some demonstrative embodiments, device 102 may perform one or more operations, for example, to calibrate a display size, for example, of display 130, e.g., as described below.

In some demonstrative embodiments, calibration of the display 130 may be performed, for example, by capturing an image of an object with a known size, placed against the display.

In some demonstrative embodiments, the object with known size may be a standard magnetic card, a CD media, a ruler, a battery (AA, AAA . . . ) and/or the like.

In some demonstrative embodiments, the object with known size may be the eyeglasses temple arm length. The arm length is typically 13.5 cm to 15 cm. This accuracy may be enough for further estimations.

In some demonstrative embodiments, the temple arm length may be scribed on an arm of the eyeglasses and the length may be used for the display calibration.

In some demonstrative embodiments, calibrating the display may include comparing an object with known dimensions to a displayed feature having a known amount of pixels.

In some demonstrative embodiments, a scaling factor, denoted scaling, may be determined, e.g., as follows:

$$\text{scaling} = \frac{S_{captured \cdot pixels}}{ref_{captured \cdot pixels}} * \frac{L_{absolute \cdot dim}}{S_{displayed \ pixels}} [\text{mm/pixel}] \quad (20)$$

In some demonstrative embodiments, a scaling of the display may be applied to display a feature having absolute size on the display.

In some demonstrative embodiments, calibration of the display may be performed, for example, by capturing an image of the display 130 at a known distance, while considering the effective focal length of the camera lens, and/or the field of view of the lens of the camera or the sensor pitch.

In some demonstrative embodiments, the magnification, denoted M, of an image having a size h of an object of size H, positioned at a camera distance L from the camera having a focal length f, may be determined, e.g., as follows:

$$M \equiv \frac{h}{H} = \frac{f}{L} \quad (21)$$

In some demonstrative embodiments, am actual size h of the image on the device may be calculated, for example, based on a sensor pitch p[μm/pixel], e.g., as follows:

$$h = h_{pix} \cdot p \quad (22)$$

wherein $h_{pix}$ is the number of pixels the image span on the device.

In some demonstrative embodiments, the absolute size H of the image on the display may be determined, e.g., as follows:

$$H = \frac{p \cdot h_{pix} L}{f} \quad (23)$$

In some demonstrative embodiments, once the displayed object with dimension of H has been determined, a scaling to the display can be applied to display a known absolute size of features on the display.

In another embodiment, the scaling factor may be considered when evaluating images from the display, without scaling the image being displayed on the display.

For example, a screen having a width of 375 mm may accommodate 1024 pixels for this dimension. A calibration object of 100 pixels may be displayed on the display and may be captured with a camera. A known size object ("a reference object") having a dimension of 300 mm may be placed on the display.

In some demonstrative embodiments, an image analysis of an image including the image of the calibration object and the image of the reference object, may show that the reference object accommodates 120 pixels and the calibration object accommodates 60 pixels. Accordingly, the scaling factor may be 1.5 mm/pixel.

In some demonstrative embodiments, the image presented on the display may be scaled, for example, to match the predetermined known size object.

In one example, in order to display an image having a dimension of 60 mm, an image having 40 pixels should be displayed.

In another example, the same amount of pixels on every screen may be displayed, and the scaling factor may be considered, for example, when capturing an image. According to this example, the scaling factor may be considered to evaluate the absolute dimension of an object, e.g., that has been displayed on the display.

Figure 16:
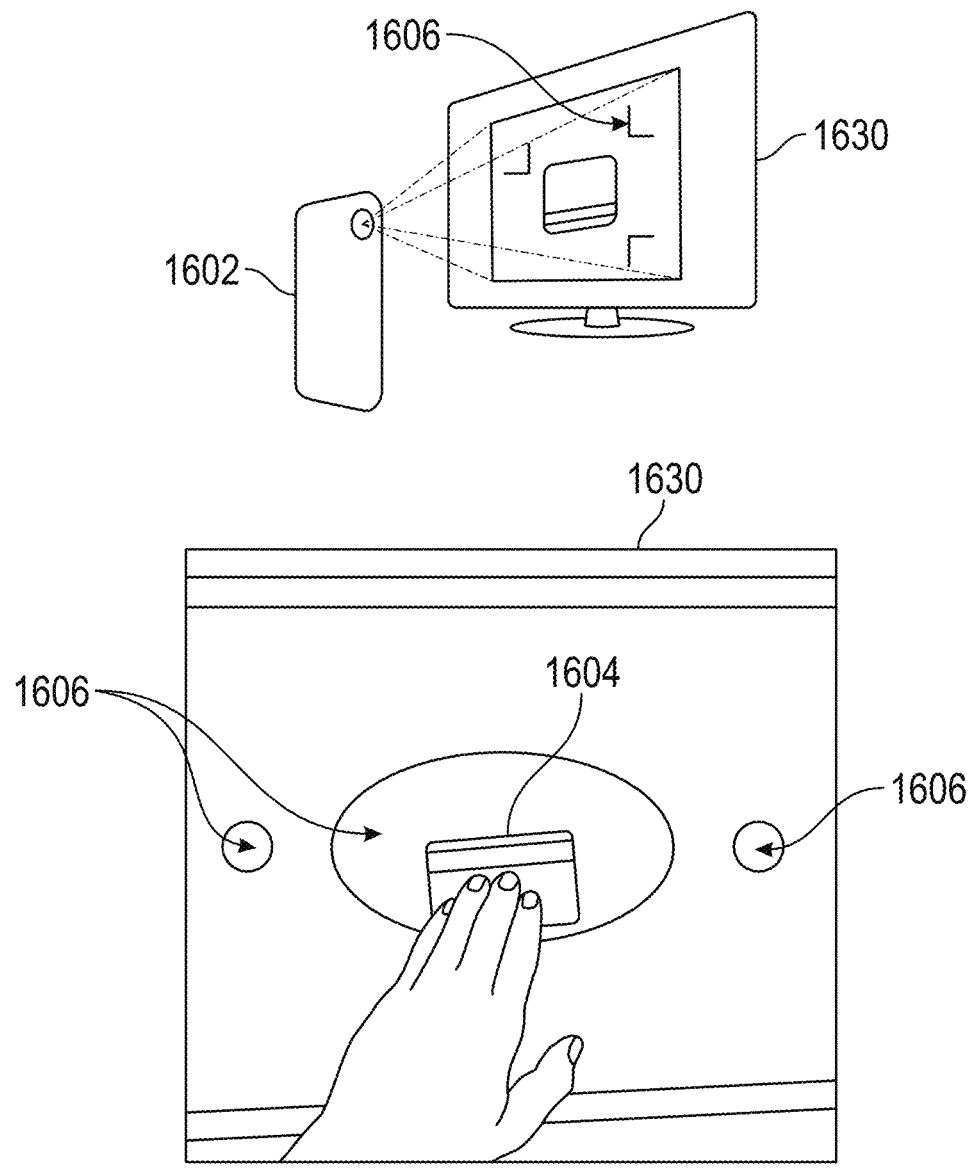
FIG. 16 is a schematic illustration of a calibration scheme, in accordance with some demonstrative embodiments.

Reference is made to FIG. 16, which schematically illustrates a calibration scheme 1600, in accordance with some demonstrative embodiments. For example, calibration scheme 1600 may be implemented to calibrate display 130 (FIG. 1).

In some demonstrative embodiments, as shown in FIG. 16, a reference object 1604, e.g. a credit card, may be placed against a display 1630.

In other embodiments, the reference object 1604 may include extended eyeglasses temple arms placed against the display.

In some demonstrative embodiments, an image capturing device 1602, e.g., camera 118 (FIG. 1), may capture an image of the reference object 1604.

In some demonstrative embodiments, as shown in FIG. 16, the display 1630 may be triggered, e.g., by application 160 (FIG. 1), display one or more calibration objects 1606, e.g., an ellipsoid or borderline shapes.

In some demonstrative embodiments, a pixel to millimeter ratio of display 1630 may be determined, for example, by comparing the reference object 1604 to the calibration objects 1606, e.g., as described above.

In some demonstrative embodiments, the calibration objects 1606 may be constituted from different channels of colors, e.g., Red-Green-Blue, so that the auto identification of the feature and the object can be utilized.

Referring back to FIG. 1, In some demonstrative embodiments, application 160 may be configured to analyze one or more parameters, visual effects, optical effects and/or attributes with respect to the image of a calibration object, e.g., displayed on display 130.

In some demonstrative embodiments, the calibration object may include a shape and/or color.

In some demonstrative embodiments, device 102 may perform an analysis for a magnification of the shape for a certain angle corresponding to a focal power at the same angle.

In some demonstrative embodiments, a spherical lens may create, for example, a uniform magnification at all angles.

In some demonstrative embodiments, a cylindrical lens may cause, for example, maximum magnification at an angle corresponding to the angle of the cylindrical lens, and no relative magnification at the angle perpendicular to the cylindrical angle.

In some demonstrative embodiments, a combination of a spherical lens and a cylindrical lens may create, for example, two perpendicular angles in which different relative magnification are apparent.

In some demonstrative embodiments, angles corresponding to the angle of the cylinder, and the magnification on each angle may be the basis for focal length calculation.

In some demonstrative embodiments, a result of two focal powers may be shown, for example, due to the cylindrical lens.

In some demonstrative embodiments, the difference between the two focal powers may be considered as the cylindrical power.

Figure 17:
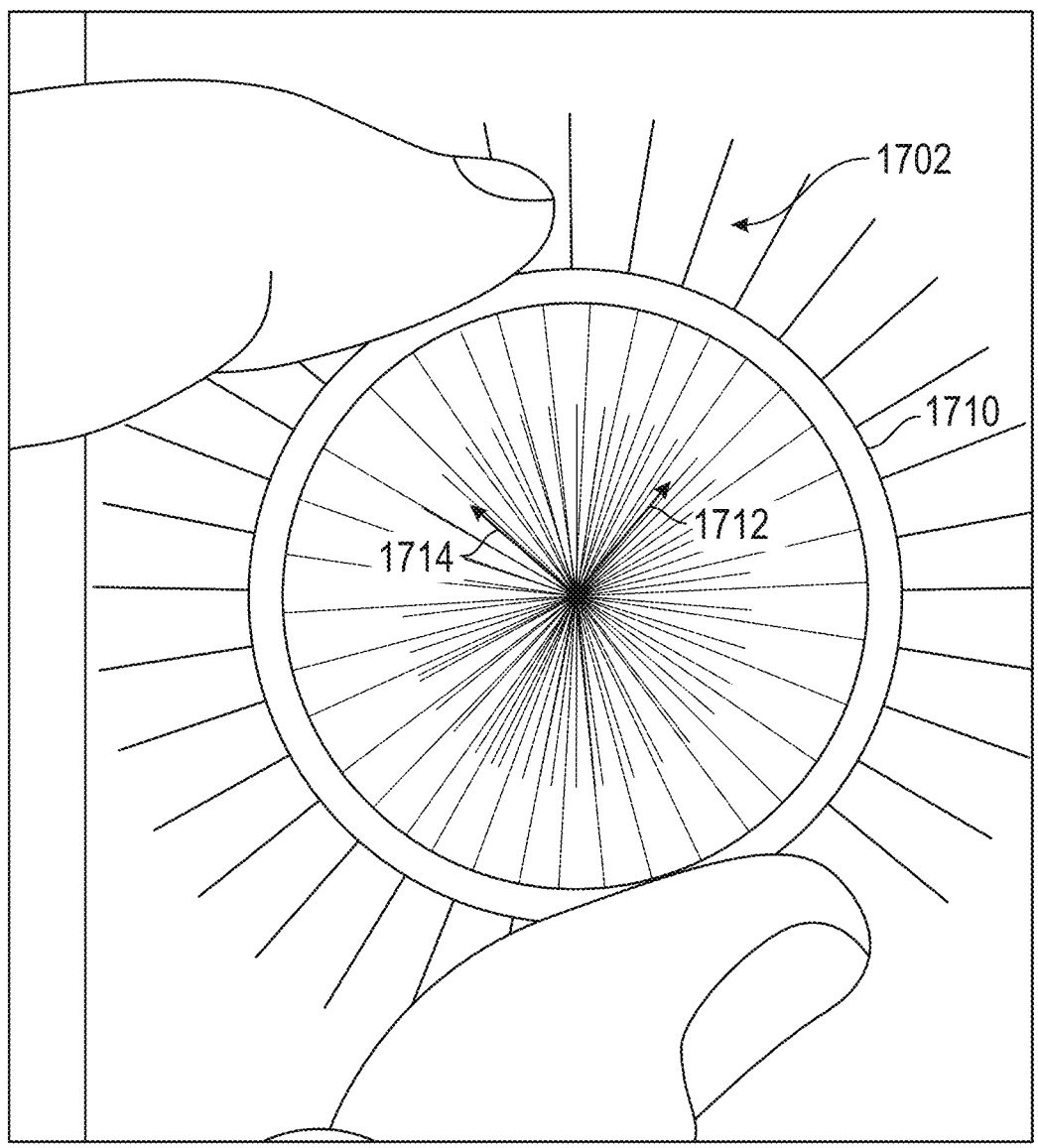
FIG. 17 is a schematic illustration of an image of an object, in accordance with some demonstrative embodiments.

Reference is made to FIG. 17, which schematically illustrates an image 1700 of an object 1702 captured via a lens 1710, in accordance with some demonstrative embodiments.

For example, application 160 (FIG. 1) may be configured to determine one or more parameters of lens 1710 based on the image of object 1102.

In some demonstrative embodiments, as shown in FIG. 17, image 1700 may illustrate the effect of magnification of two focal powers of lens 1710.

In some demonstrative embodiments, as shown in FIG. 17, object 1702 may be composed of radial lines in several radii.

In some demonstrative embodiments, as shown in FIG. 17, the two focal powers of a lens 1710 may create two magnifications.

In some demonstrative embodiments, as shown in FIG. 17, since both powers are negative, the two focal powers of a lens 1710 may create two minifications.

In some demonstrative embodiments, as shown in FIG. 17, measuring the length of each radial line in every angle, may demonstrate that the length varies, which is the effect of the magnification of two focal powers that are perpendicular to one another.

In some demonstrative embodiments, as shown in FIG. 17, this effect may create lines in the image that show a maximal magnification at an angle 1712, and a minimal magnification at a perpendicular angle 1714.

In some demonstrative embodiments, these two magnifications may be used, e.g., by application 160 (FIG. 1), to determine the two focal powers, and the angle at which the largest magnification occurs may be used, for example, by application 160 (FIG. 1), to determine the angle of the cylinder.

In some demonstrative embodiments, as shown in FIG. 17, a circular symmetric object can be utilized as object 1702. In this case the image may go through a magnification change, which for cylindrical lens, will result in an elliptical shape.

In some demonstrative embodiments, lens power, lens cylinder power and/or cylinder angle can be extracted, e.g., by application 160 (FIG. 1), for example, by studying total magnification, and the ratio between the long and short ellipse axes and the ellipse angle.

Figure 18:
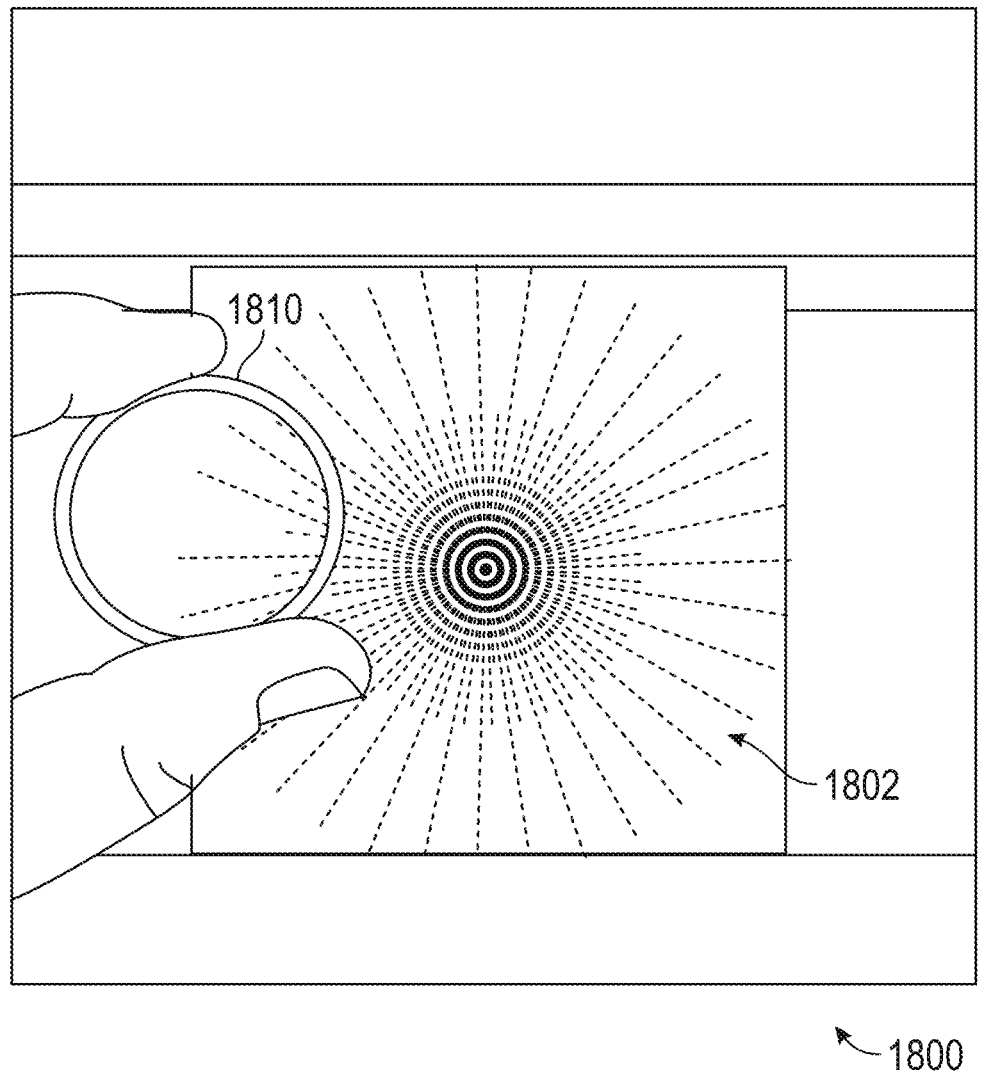
FIG. 18 is a schematic illustration of an image of an object, in accordance with some demonstrative embodiments.

Reference is made to FIG. 18, which schematically illustrates an image 1800 of an object 1802, in accordance with some demonstrative embodiments.

In some demonstrative embodiments, as shown in FIG. 18, object 1802 may be partially captured via a lens 1810, e.g., while other portions of object 1802 may be captured not thorough lens 1810.

For example, application 160 (FIG. 1) may be configured to determine one or more parameters of lens 1810 based on the image of object 1802.

In some demonstrative embodiments, as shown in FIG. 18, object 1802 may include an object, which may be composed of radial lines in several radii, each line may be composed of a dashed line and different radii may be designated by different colors or different line types.

In some demonstrative embodiments, the use of object 1802, e.g., including the dashed line, may assist to determine the magnification, for example, since the spatial frequency of each line changes under different magnification.

Figure 19:
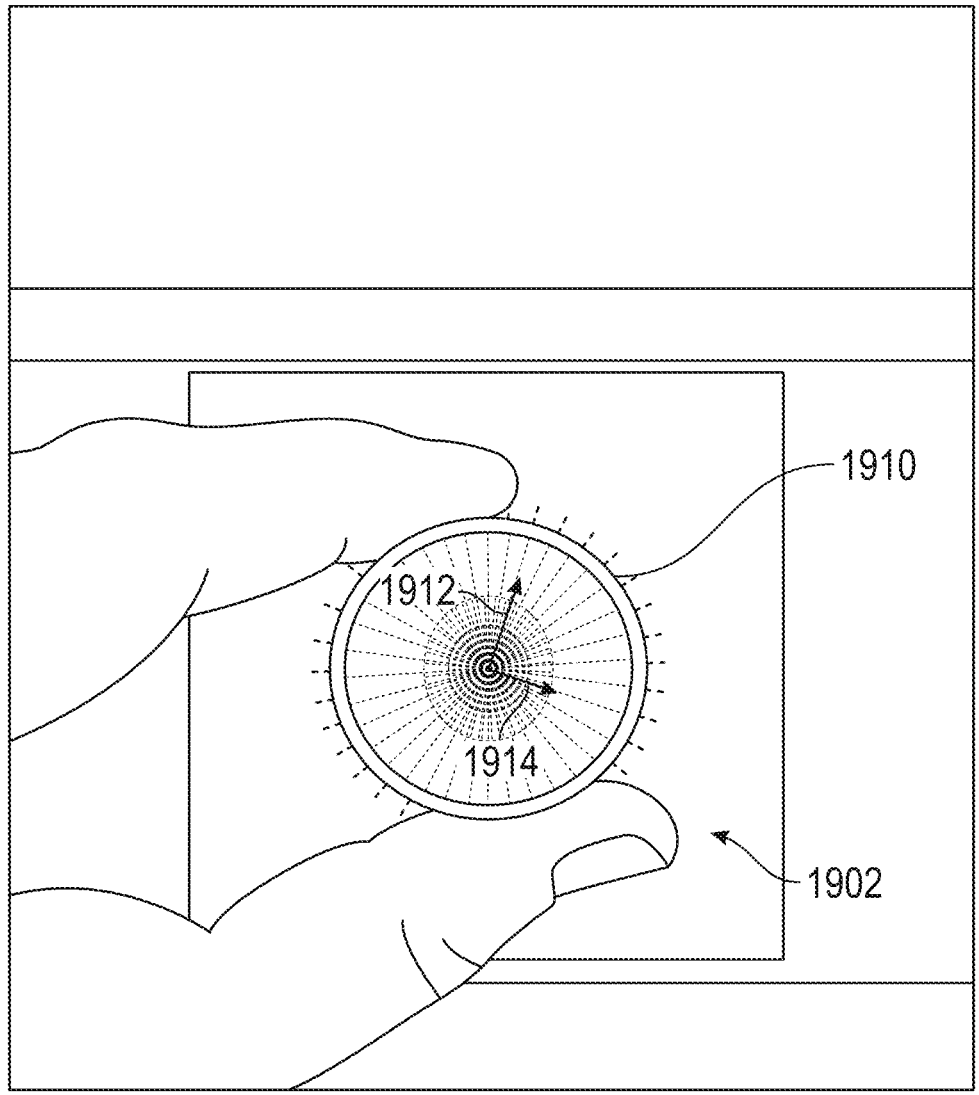
FIG. 19 is a schematic illustration of an image of an object, in accordance with some demonstrative embodiments.

Reference is made to FIG. 19, which schematically illustrates an image 1900 of an object 1902 captured via a lens 1910, in accordance with some demonstrative embodiments. For example, application 160 (FIG. 1) may be configured to determine one or more parameters of lens 1910 based on the image of object 1902.

In some demonstrative embodiments, as shown in FIG. 19, lens 1910 may include a spherical and cylindrical lens.

In some demonstrative embodiments, as shown in FIG. 19, the captured image 1900 of object 1902 may illustrate a change of magnification that creates a maximum magnification at an angle 1912, and a minimum magnification at a perpendicular angle 1914.

In some demonstrative embodiments, as shown in FIG. 19, the captured image 1900 may illustrate a spatial frequency in lines at different meridians, which may be caused by a different magnification per meridian.

In some demonstrative embodiments, it may be apparent that the cylindrical effect causes the equal radial lines to create an elliptical shape.

Figure 20:
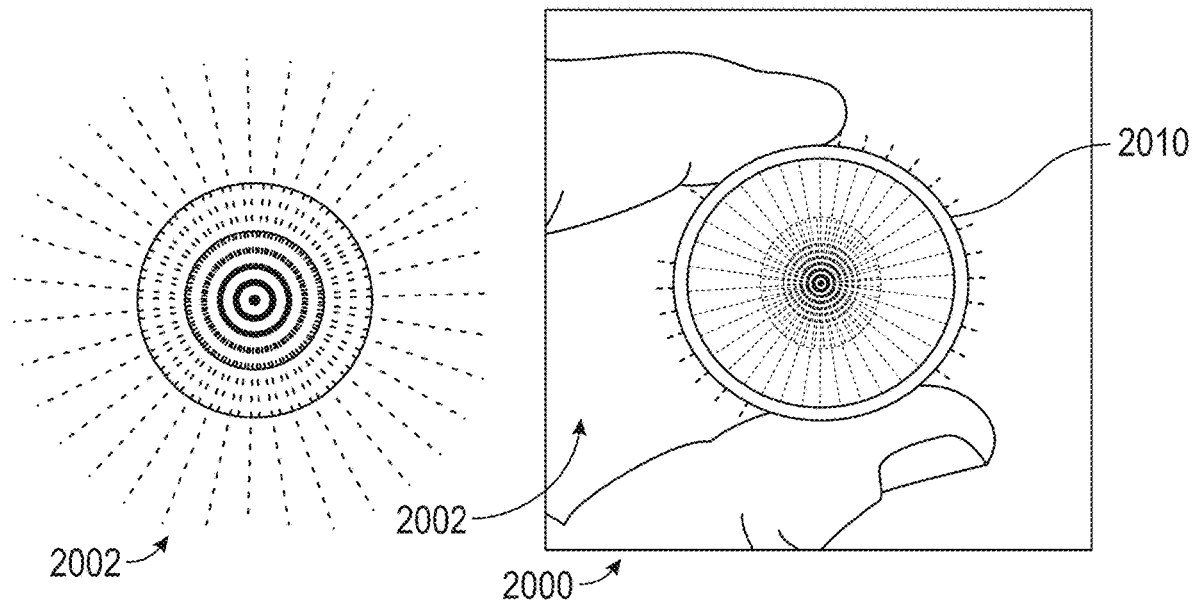
FIG. 20 is a schematic illustration of an image of an object, in accordance with some demonstrative embodiments.

Reference is made to FIG. 20, which schematically illustrates an image 2000 of an object 2002 captured via a lens 2010, in accordance with some demonstrative embodiments.

For example, application 160 (FIG. 1) may be configured to determine one or more parameters of lens 2010 based on the image of object 2002.

In some demonstrative embodiments, as shown in FIG. 20, object 2002 may include outlining of a line connecting all lines with the same radii.

In some demonstrative embodiments, as shown in FIG. 20, image 2000 may show how different perpendicular focal powers of lens 2010 may create two perpendicular magnifications that transform a circular shape into an elliptical shape.

In some demonstrative embodiments, as shown in FIG. 20, the largest magnification may occur at an angle 2012, e.g., the cylindrical axis, and the minimum magnification may occur at a perpendicular angle 2014.

In some demonstrative embodiments, as shown in FIG. 20, the orientation of lens 2010 may be taken under consideration to calculate the absolute axis of the cylinder. For each of the ellipse axes the relative magnification may be determined, and then the power of the lens may be determined.

In some demonstrative embodiments, due to different magnifications, for example, due to a power of lens 2010, the object 2002 may be displayed at different scales on image 2000.

In some demonstrative embodiments, displaying several concentric circular rings each with a different radius may enable to analyze both positive and negative magnification at different powers.

In some demonstrative embodiments, the magnification and cylinder in these concentric rings may be further analyzed, using, for example, a Fourier transform, e.g., by tracking the dominant frequency along different directions.

In some demonstrative embodiments, using several objects may provide the advantage of improving accuracy, e.g., by averaging.

In other embodiments, object 2002 may include a dense grid line.

In some demonstrative embodiments, lens power, cylinder and aberrations can be deduced, for example, by following the distortion within the dense grid line.

In some demonstrative embodiments, object 2002 may include chromo effects, for example, to enable identifying certain features in image 200. For example, a minor defocus of colors, e.g., such as green and red, may result in a yellow color, e.g., where the two colors are adjacent.

Referring back to FIG. 1, in some demonstrative embodiments, application 160 may be configured to determine that an image captured via the lens is captured through the center of the lens.

In some demonstrative embodiments, application 160 may be configured to perform one or more operations, methods and/or procedure to ensure that a minimum displacement from the center of the lens an image captured via the lens.

Figure 21:
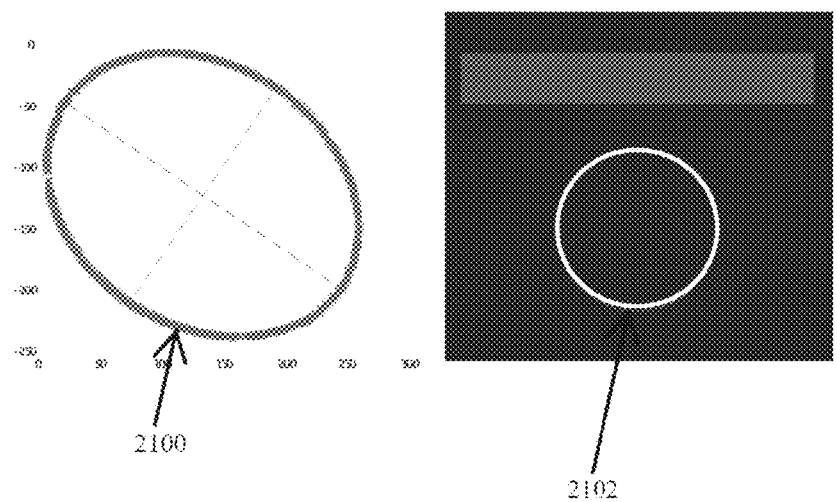
FIG. 21 is a schematic illustration of an ellipse curve fit of a circular ring object, in accordance with some demonstrative embodiments.

Reference is made to FIG. 21, which schematically illustrates an ellipse curve fit 2100 of a circular ring object 2102, in accordance with some demonstrative embodiments.

In some demonstrative embodiments, ellipse curve fit 2100 may result from capturing circular ring object 2102, for example, via a cylindrical lens.

In some demonstrative embodiments, as shown in FIG. 21, an ellipse curve fit 2102 of a circular ring object image 2100 may be captured through a cylindrical test lens.

Referring back to FIG. 1, in some demonstrative embodiments, application 160 may be configured to determine the one or more optical parameters of a lens, for example, even without using display 130. For example, application 160 may be configured to determine a cylindrical power, and/or a cylinder angle and/or a spherical power of the lens, for example, even without using display 130, e.g., as described below.

In some demonstrative embodiments, application 160 may be configured to determine the one or more optical parameters of a lens, for example, even without displaying an image on display 130.

In some demonstrative embodiments, application 160 may be configured to determine the one or more optical parameters of a lens, for example, based on a captured image of an object having a known size, e.g., as described below.

In some demonstrative embodiments, the one or more optical parameters of the lens such as sphere power, cylinder power and/or cylinder angle may be found, for example, by using a camera or a Smartphone device and an object of a known size.

In some demonstrative embodiments, by capturing an image of the object of known size through the lens, the one or more optical parameters of the lens may be found.

In some demonstrative embodiments, the object of known size may include, for example, a coin having a known size, an Iris of the eye or a calibrated iris diameter of the eye, and/or any other object or element.

In some demonstrative embodiments, using the calibration object may allow determining the one or more optical parameters of a lens, for example, even without using a screen to display an object, and/or even without calibration prior to measurement of the one or more optical parameters of the lens.

In some demonstrative embodiments, the lens power and/or cylinder parameters may be deduced from a deformation of the observed image of the calibration object through the tested lens relative to an image of the calibration object, which may be observed directly without the test lens.

In some demonstrative embodiments, spectacle eyeglasses parameters, e.g., a sphere power, a cylinder power and/or a cylinder angle, may be determined, for example, using a camera or a Smartphone device, e.g., even without using an external object of known size.

In some demonstrative embodiments, by capturing an image of an eye of a wearer of the eyeglasses, it may be possible to analyze a change in an Iris size of the Iris of the wearer resulting from the spectacle eyeglasses. For example, an image of the Iris with and without the eyeglasses may be compared and analyzed, e.g., to determine the spectacle eyeglasses parameters.

In some demonstrative embodiments, if needed, a cornea absolute size may be calibrated, for example, using a known size object, e.g., a coin or a credit card.

Referring back to FIG. 1, in some demonstrative embodiments, application 160 may be configured to determine a pupillary distance (PD) between a first lens of eyeglasses and a second lens of the eyeglasses, e.g., as described below.

In some demonstrative embodiments, application 160 may be configured to process an image of an object including a first element and a second element, e.g., as described below. In one example, application 160 may be configured to cause display 130 to display the object.

In some demonstrative embodiments, the image may include a first imaged element of the first element captured via the first lens and a second imaged element of the second element captured via the second lens.

In some demonstrative embodiments, application 160 may be configured to determine the pupillary distance between the first and second lenses, for example, based on at least a first distance between the first and second elements, and a second distance between the first and second imaged elements, e.g., as described below.

Figure 22:
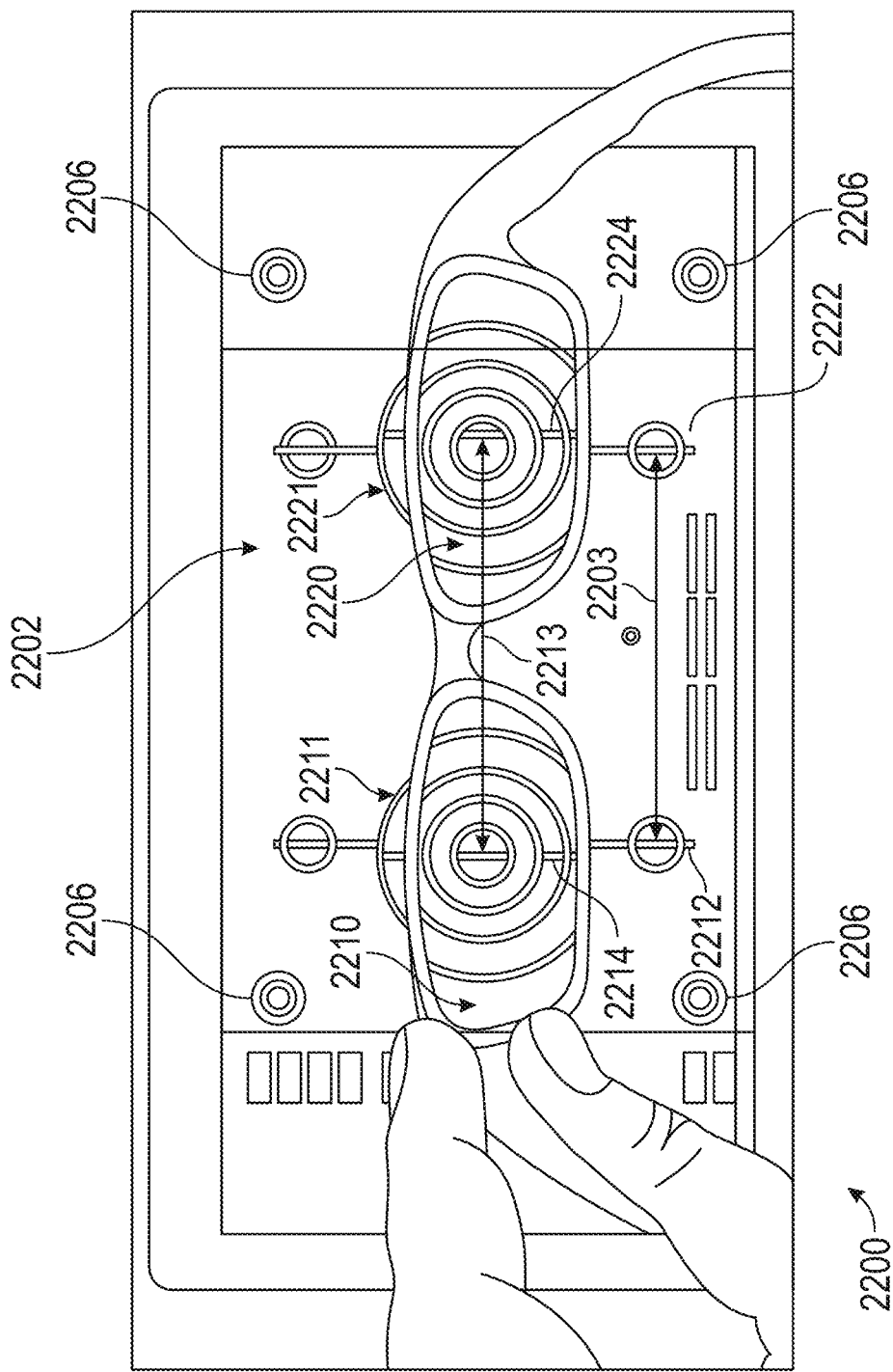
FIG. 22 is a schematic illustration of an image of an object captured via two lenses of eyeglasses, in accordance with some demonstrative embodiments.

Reference is made to FIG. 22, which schematically illustrates an image 2200 of an object 2202, in accordance with some demonstrative embodiments. For example, application 160 (FIG. 1) may cause display 130 (FIG. 1) to display object 2202, and/or control camera 118 (FIG. 1) to capture image 2200.

In some demonstrative embodiments, application 160 (FIG. 1) may be configured to determine a pupillary distance between a first lens 2210 of eyeglasses and a second lens 2220 of the eyeglasses, for example, based on image 2200, e.g., as described below.

In some demonstrative embodiments, as shown in FIG. 22, object 2202 may be displayed on a display device and may include a first circularly symmetric object 2211 and a second circularly symmetric object 2221. In other embodiments, object 2202 may include any other additional or alternative shapes, objects and/or elements.

In some demonstrative embodiments, objects 2211 and 2221 may include a plurality of concentric circular rings. For example, each ring may have a different radius. In other embodiments, objects 2211 and 2221 may include any other additional or alternative shape, object and/or element.

In some demonstrative embodiments, as shown in FIG. 22, object 2202 may include a first line element 2212 and a second line element 2222.

In some demonstrative embodiments, as shown in FIG. 22, line elements 2212 and/or 2222 may include vertical line shape elements. In other embodiments, line elements 2212 and/or 2222 may include any other additional or alternative shape, object and/or element.

In some demonstrative embodiments, as shown in FIG. 22, line element 2212 may cross a center of circularly symmetric object 2211, and/or line element 2222 may cross a center of circularly symmetric object 2221.

In some demonstrative embodiments, a distance 2203 between line elements 2212 and 2222 may be preconfigured or preset. In one example, the distance 2203 may be configured based on a typical PD value or a range of PD values.

In some demonstrative embodiments, as shown in FIG. 22, image 2200 may include a first imaged element 2214 of the first element 2212 captured via the first lens 2210.

In some demonstrative embodiments, as shown in FIG. 22, image 2200 may include a second imaged element 2224 of the second element 2222 captured via the second lens 2220.

In some demonstrative embodiments, application 160 (FIG. 1) may be configured to determine the pupillary distance of the lenses 2210 and 2220 assembled in the eyeglasses, for example, based on at least a first distance 2203 between elements 2212 and 2222, and a second distance 2213 between imaged elements 2214 and 2224, e.g., as described below.

In some demonstrative embodiments, as shown in FIG. 22, line elements 2212 and/or 2222 may assist in recognizing and/or evaluating a change or difference between the distance 2213, e.g., as imaged through lenses 2210 and 2220, and the distance 2203, e.g., imaged not through lenses 2210 and 2220.

In some demonstrative embodiments, application 160 (FIG. 1) may utilize a distance of the eyeglasses from a camera, e.g., camera 118 (FIG. 1), which captures image 2202, and powers of the lenses 2210 and 2220, for example, to evaluate the PD from image 2202.

In some demonstrative embodiments, the distance 2203 may be known or calibrated, e.g., as described above.

In some demonstrative embodiments, application 160 (FIG. 1) may be configured to determine the PD of the eyeglasses including lenses 220 and 2220, for example, based on a first distance of the camera, e.g., camera 118 (FIG. 1) from the display, e.g., display 130 (FIG. 1) ("the camera-display distance"), and a second distance of lenses 2210 and 2220 from the camera ("the camera-glasses distance"), e.g., as described below.

In some demonstrative embodiments, the PD may be determined, for example, based on the camera-display distance and the camera-glasses distance, the powers of lenses 2210 and/or 2220, and/or distances 2203 and 2213.

In some demonstrative embodiments, as shown in FIG. 22, image 2202 may include one or more calibration elements 2206.

In some demonstrative embodiments, calibration elements 2206 may be captured in image 2200 not via lenses 2210 and/or 2220.

In some demonstrative embodiments, one or more features of calibration elements 2206 may be known, and/or measured. For example, distances between calibration elements 2206 may be known and/or measured, diameters of calibration elements 2206 may be known and/or measured, and/or the like.

In some demonstrative embodiments, application 160 (FIG. 1) may be configured, for example, to determine the camera-display distance, e.g., based on image 2200.

In some demonstrative embodiments, circularly symmetric objects 2211 and 2221 may be imaged simultaneously via the lenses 2210 and 2220, respectively, while the eyeglasses are located at the camera-glasses distance, e.g., when image 2200 is captured.

In some demonstrative embodiments, a relative magnification of circularly symmetric objects 2211 and 2221 in image 2202, e.g., with respect to the actual sizes of circularly symmetric objects 2211 and 2221, may be calculated, for example, to determine the spherical power and/or cylindrical power and/or axis of lenses 2210 and/or 2220, e.g., separately.

In some demonstrative embodiments, a lateral displacement of the centers of circularly symmetric objects 2211 and 2221 may be seen, for example, by displacement between line elements 2212 and/or 2222 and imaged line elements 2214 and 2224.

In some demonstrative embodiments, the lateral displacement may be derived from image 2200, for example, even without line elements 2212 and/or 2222, for example, based on the centers of circularly symmetric object 2211 and 2221, e.g., as the locations of the centers may be predefined, e.g., with respect to calibration objects 2206.

In some demonstrative embodiments, a lateral displacement of an image of an object through a lens may be determined, for example, based on one or more parameters, e.g., including a lens lateral displacement from an optical axis of the lens, a distance of the lens from the object, a distance of the camera from the object, and/or a power of the lens.

In some demonstrative embodiments, application 160 (FIG. 1) may be configured to determine the distance between the centers of the lenses 2210 and 2220, the power of the lenses 2210 and/or 2220, and/or the cylinder power and axis of the lens, e.g., simultaneously, for example, based on the one or more parameters.

In some demonstrative embodiments, the distance of the eyeglasses from the camera, e.g., the camera-glasses distance, may be determined, for example, based on a given PD of the eyeglasses, for example, using image 2200, e.g., as described below with reference to FIG. 24.

Figure 23:
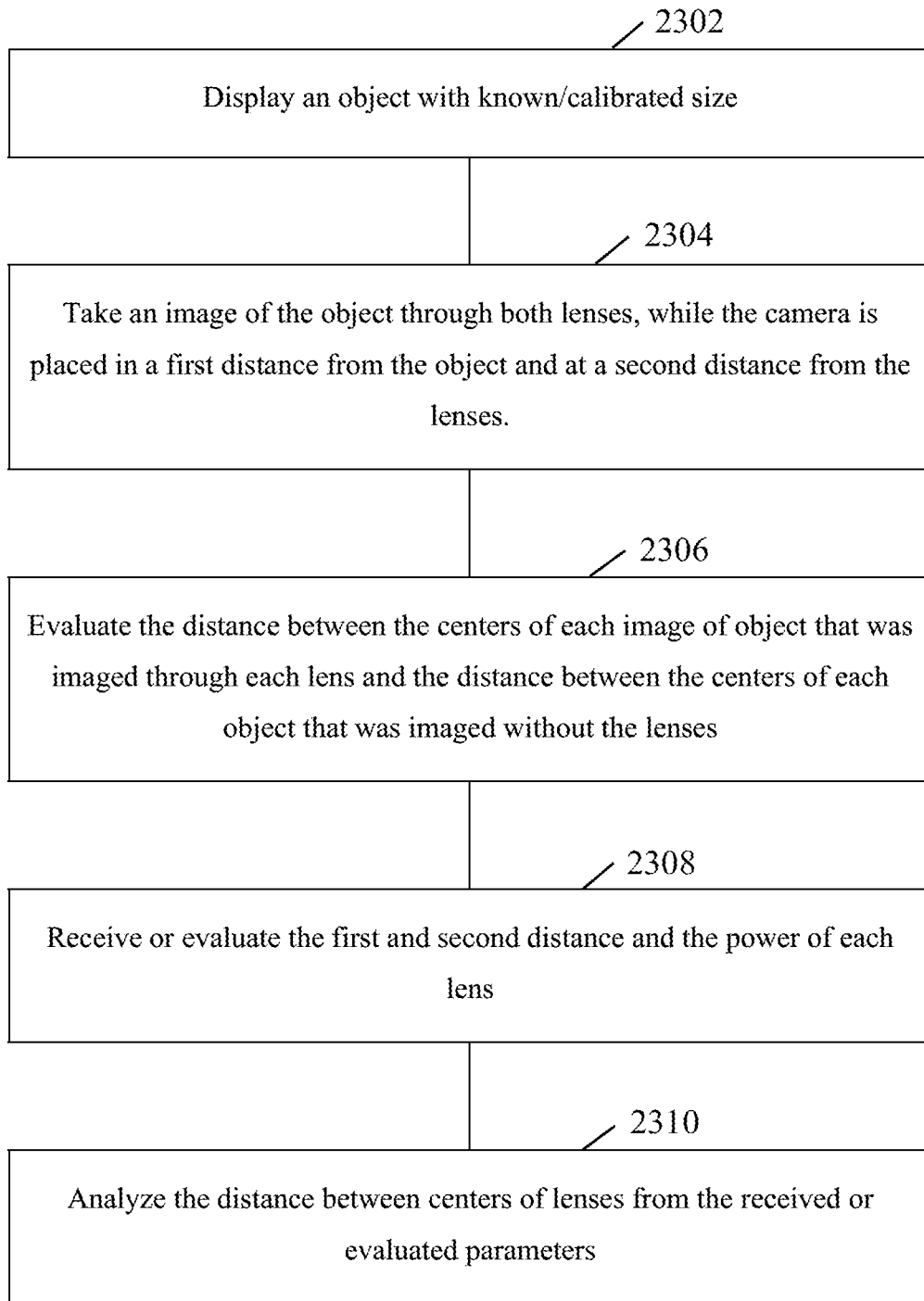
FIG. 23 is a schematic flow-chart illustration of a method of determining a pupillary distance of lenses of eyeglasses, in accordance with some demonstrative embodiments.

Reference is made to FIG. 23, which schematically illustrates a method of determining a pupillary distance of lenses of eyeglasses, in accordance with some demonstrative embodiments. For example, one or operations of the method of FIG. 23 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 2302, the method may include displaying an object having one or more known or calibrated sizes on a display. For example, application 160 (FIG. 1) may cause display 130 (FIG. 1) to display object 2202 (FIG. 22), e.g., as described above.

As indicated at block 2304, the method may include capturing an image of the object through both lenses of the eyeglasses with a camera, while the camera is placed at a first distance from the object and at a second distance from the lenses. For example, application 160 (FIG. 1) may cause camera 118 (FIG. 1) to capture the image 2200 (FIG. 22) of object 2202 (FIG. 22) via lenses 2210 and 2220 (FIG. 22), for example, while the camera 118 (FIG. 1) is at the camera-display distance and the lens is at the camera-glasses distance, e.g., as described above.

As indicated at block 2306, the method may include determining the distance between imaged centers of the object imaged through each lens, and the distance between the centers of the object imaged without the lenses. For example, application 160 (FIG. 1) may be configured to determine the distance 2213 (FIG. 22) and the distance 2203 (FIG. 22), e.g., as described above.

As indicated at block 2308, the method may include receiving and/or determining one or more parameters to enable a PD calculation, e.g., the first distance, the second distance, and/or the power of each lens. For example, application 160 (FIG. 1) may receive and/or determine the camera-display distance, the camera-glasses distance, and/or the powers of lenses 2210 and 2220 (FIG. 22), e.g., as described above.

As indicated at block 2310, the method may include determining the distance between centers of the lenses, based on the one or more parameters. For example, application 160 (FIG. 1) may determine the PD of the eyeglasses, for example, based on the camera-glasses distance, the camera-display distance, and/or the powers of lenses 2210 and 2220 (FIG. 22), e.g., as described above.

Referring back to FIG. 1, in some demonstrative embodiments, application 160 may be configured to determine a distance between camera 118 and the eyeglasses ("the camera-lens distance"), for example, based on a pupillary distance between lenses of the eyeglasses, e.g., as described below.

Figure 24:
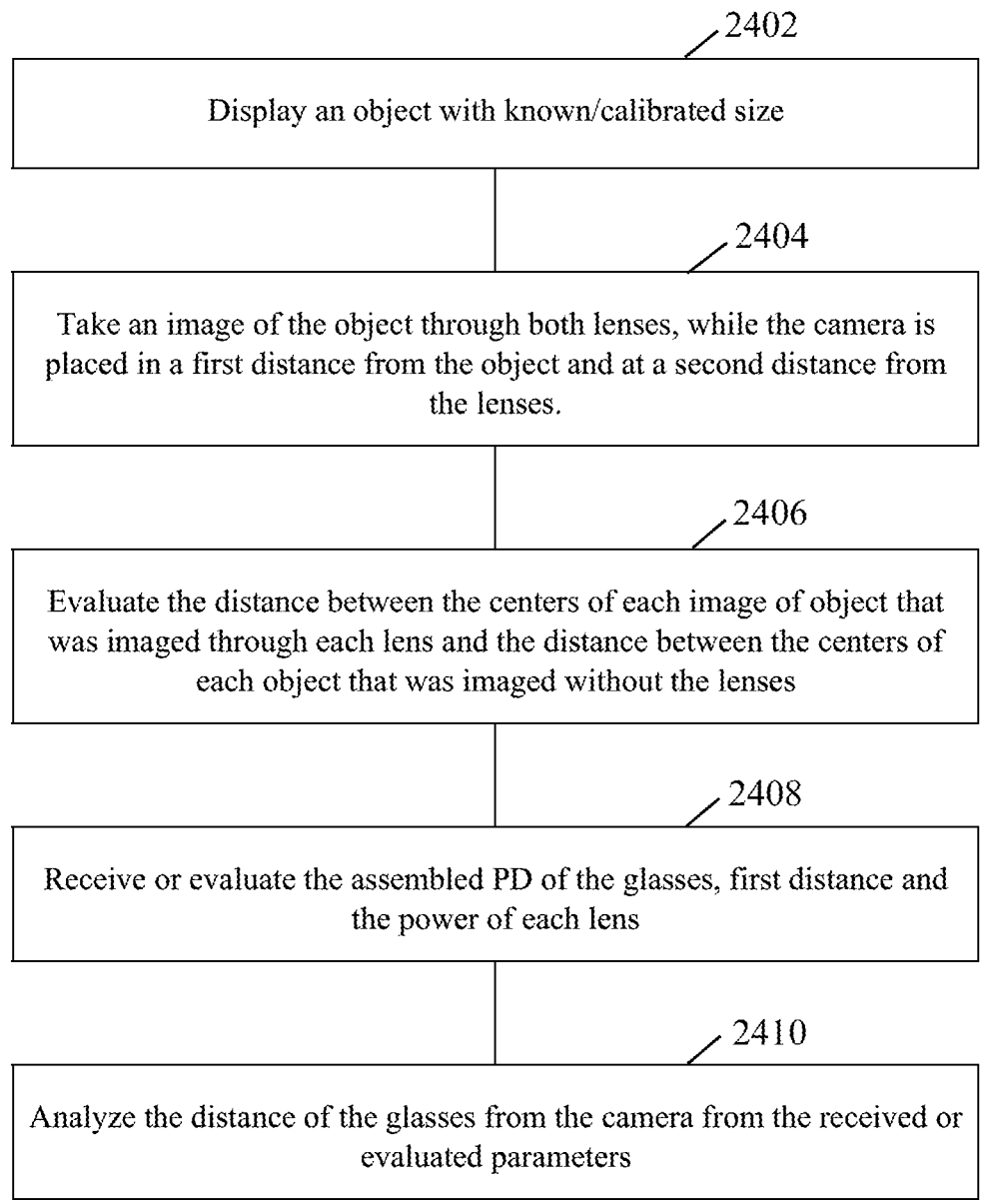
FIG. 24 is a schematic flow-chart illustration of a method of determining a distance between a camera and eyeglasses, in accordance with some demonstrative embodiments.

Reference is made to FIG. 24, which schematically illustrates a method of determining a distance between a camera and eyeglasses, in accordance with some demonstrative embodiments. For example, one or operations of the method of FIG. 24 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, application 160 (FIG. 1) may perform one or more operations of FIG. 24 to determine the camera-lenses distance, for example, based on an estimated or preconfigured pupillary distance of the lenses of the eyeglasses.

As indicated at block 2402, the method may include displaying an object having one or more known or calibrated sizes on a display. For example, application 160 (FIG. 1) may cause display 130 (FIG. 1) to display object 2202 (FIG. 22), e.g., as described above.

As indicated at block 2404, the method may include capturing an image of the object through both lenses of the eyeglasses with a camera, while the camera is placed at a first distance from the object and at a second distance from the lenses. For example, application 160 (FIG. 1) may cause camera 118 (FIG. 1) to capture the image 2200 (FIG. 22) of object 2202 (FIG. 22) via lenses 2210 and 2220 (FIG. 22), for example, while the camera 118 (FIG. 1) is at the camera-display distance and the lens is at the camera-glasses distance, e.g., as described above.

As indicated at block 2406, the method may include determining the distance between imaged centers of the object imaged through each lens, and the distance between the centers of the object imaged without the lenses. For example, application 160 (FIG. 1) may be configured to determine the distance 2213 (FIG. 22) and the distance 2203 (FIG. 22), e.g., as described above.

As indicated at block 2408, the method may include receiving and/or determining one or more parameters, e.g., the PD of the eyeglasses, the first distance, and/or the power of each lens. For example, application 160 (FIG. 1) may receive and/or determine the camera-display distance, the PD of the eyeglasses, and/or the powers of lenses 2210 and 2220 (FIG. 22), e.g., as described above.

As indicated at block 2410, the method may include determining the camera-lens distance, based on the one or more parameters. For example, application 160 (FIG. 1) may determine the camera-glasses distance, for example, based on the camera-display distance, the PD of the eyeglasses, and/or the powers of lenses 2210 and 2220 (FIG. 22), e.g., as described above.

Figure 25:
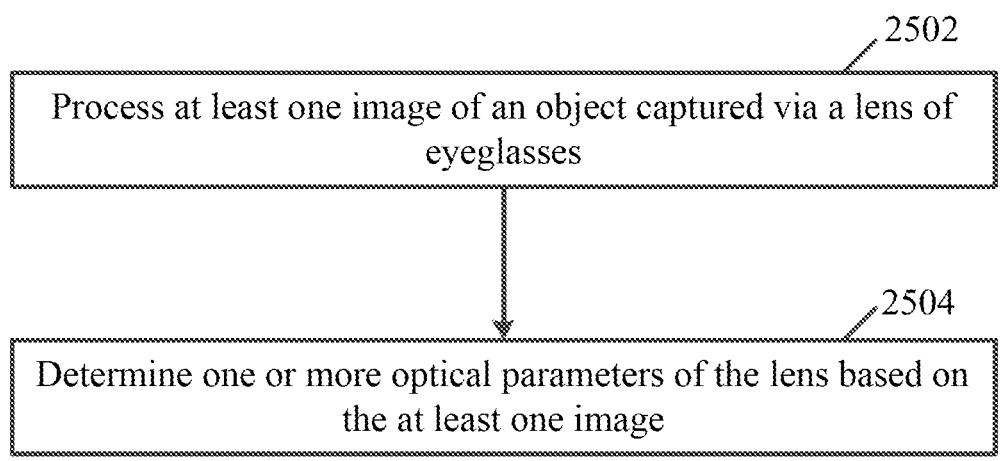
FIG. 25 is a schematic flow-chart illustration of a method of determining one or more optical parameters of a lens, in accordance with some demonstrative embodiments.

Reference is made to FIG. 25, which schematically illustrates a method of determining one or more optical parameters of a lens, in accordance with some demonstrative embodiments. For example, one or operations of the method of FIG. 22 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 2502, the method may include processing at least one image of an object captured via the lens. For example, application 160 (FIG. 1) may process the at least one image captured via the lens of the object displayed over display 130 (FIG. 1), e.g., as described above.

As indicated at block 2504, the method may include determining the one or more optical parameters of the lens based on the at least one image. For example, application 160 (FIG. 1) may determine the one or more optical parameters of the lens based on the at least one image, e.g., by performing one or more operations as described above with respect to one or more of FIGS. 1-21.

Figure 26:
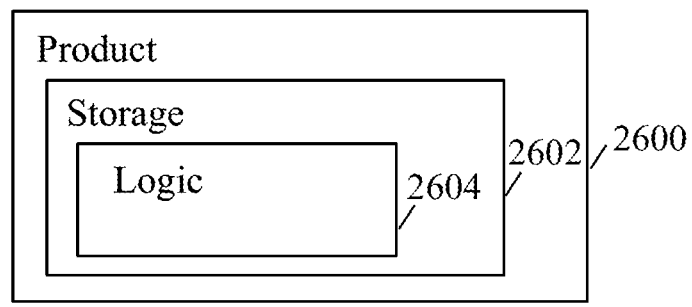
FIG. 26 is a schematic illustration of a product, in accordance with some demonstrative embodiments.

Reference is made to FIG. 26, which schematically illustrates a product of manufacture 2600, in accordance with some demonstrative embodiments. Product 2600 may include one or more tangible computer-readable non-transitory storage media 2302, which may include computer-executable instructions, e.g., implemented by logic 2604, operable to, when executed by at least one computer processor, enable the at least one computer processor to implement one or more operations at device 102 (FIG. 1), server 170 (FIG. 1), display 130 (FIG. 1), and/or application 160 (FIG. 1), and/or to perform, trigger and/or implement one or more operations, communications and/or functionalities according to one or more FIGS. 1-25, and/or one or more operations described herein. The phrase "non-transitory machine-readable medium" is directed to include all computer-readable media, with the sole exception being a transitory propagating signal.

In some demonstrative embodiments, product 2600 and/or machine-readable storage medium 2602 may include one or more types of computer-readable storage media capable of storing data, including volatile memory, non-volatile memory, removable or non-removable memory, erasable or non-erasable memory, writeable or re-writeable memory, and the like. For example, machine-readable storage medium 2302 may include, RAM, DRAM, Double-Data-Rate DRAM (DDR-DRAM), SDRAM, static RAM (SRAM), ROM, programmable ROM (PROM), erasable programmable ROM (EPROM), electrically erasable programmable ROM (EEPROM), Compact Disk ROM (CD-ROM), Compact Disk Recordable (CD-R), Compact Disk Rewriteable (CD-RW), flash memory (e.g., NOR or NAND flash memory), content addressable memory (CAM), polymer memory, phase-change memory, ferroelectric memory, silicon-oxide-nitride-oxide-silicon (SONOS) memory, a disk, a floppy disk, a hard drive, an optical disk, a magnetic disk, a card, a magnetic card, an optical card, a tape, a cassette, and the like. The computer-readable storage media may include any suitable media involved with downloading or transferring a computer program from a remote computer to a requesting computer carried by data signals embodied in a carrier wave or other propagation medium through a communication link, e.g., a modem, radio or network connection.

In some demonstrative embodiments, logic 2604 may include instructions, data, and/or code, which, if executed by a machine, may cause the machine to perform a method, process and/or operations as described herein. The machine may include, for example, any suitable processing platform, computing platform, computing device, processing device, computing system, processing system, computer, processor, or the like, and may be implemented using any suitable combination of hardware, software, firmware, and the like.

In some demonstrative embodiments, logic 2604 may include, or may be implemented as, software, a software module, an application, a program, a subroutine, instructions, an instruction set, computing code, words, values, symbols, and the like. The instructions may include any suitable type of code, such as source code, compiled code, interpreted code, executable code, static code, dynamic code, and the like. The instructions may be implemented according to a predefined computer language, manner or syntax, for instructing a processor to perform a certain function. The instructions may be implemented using any suitable high-level, low-level, object-oriented, visual, compiled and/or interpreted programming language, such as C, C++, Java, BASIC, Matlab, Pascal, Visual BASIC, assembly language, machine code, and the like.

EXAMPLES

The following examples pertain to further embodiments.

Example 1 includes a product comprising one or more tangible computer-readable non-transitory storage media comprising computer-executable instructions operable to, when executed by at least one computer processor, enable the at least one computer processor to implement operations of determining one or more optical parameters of a lens of eyeglasses, the operations comprising processing at least one image of an object captured via the lens; and determining the one or more optical parameters of the lens based on the at least one image.

Example 2 includes the subject matter of Example 1, and optionally, wherein the operations comprise determining the one or more optical parameters of the lens based on a magnification between at least one imaged dimension of the object in the image and at least one respective reference dimension of the object.

Example 3 includes the subject matter of Example 2, and optionally, wherein the operations comprise determining a spherical power of the lens based on the magnification.

Example 4 includes the subject matter of Example 2 or 3, and optionally, wherein the operations comprise determining a cylindrical axis of the lens based on a maximal magnification axis of a plurality of axes in the image, at which a magnification between the imaged dimension and the reference dimension is maximal.

Example 5 includes the subject matter of Example 4, and optionally, wherein the operations comprise determining the cylindrical power of the lens based on the maximal magnification axis and a minimal magnification axis of the plurality of axes in the image, at which a magnification between another imaged dimension and another respective reference dimension of the object is minimal.

Example 6 includes the subject matter of Example 5, and optionally, wherein the operations comprise determining the cylindrical power of the lens based on a first magnification at the minimal magnification axis, and a second magnification at the maximal magnification axis.

Example 7 includes the subject matter of any one of Examples 2-6, and optionally, wherein the operations comprise determining the one or more optical parameters of the lens based on the magnification, and another magnification of at least one dimension in an image of a calibration object having known dimensions, the image of the calibration object is captured not via the lens.

Example 8 includes the subject matter of any one of Examples 1-7, and optionally, wherein a distance between the object and the lens when the image is captured is half of a distance between the object and an image-capturing device when the image is captured.

Example 9 includes the subject matter of any one of Examples 1-8, and optionally, wherein the operations comprise determining the one or more optical parameters of the lens based on a first distance between the object and an image-capturing device when the image is captured, and a second distance between the object and the lens when the image is captured.

Example 10 includes the subject matter of Example 9, and optionally, wherein the second distance comprises a distance between the object and the lens when temple arms of the eyeglasses are extended to a plane of the object.

Example 11 includes the subject matter of Example 9, and optionally, wherein the operations comprise processing a plurality of images of the object captured via the lens at a respective plurality of first distances, while the second distance is constant, determining an extremum magnification image of the plurality of images, in which a magnification between the imaged dimension and the reference dimension is extremum, and determining the one or more optical parameters of the lens based on the extremum magnification image.

Example 12 includes the subject matter of Example 9, and optionally, wherein the operations comprise processing a plurality of images of the object captured via the lens at a respective plurality of second distances, while the first distance is constant, determining an extremum magnification image of the plurality of images, in which a magnification between the imaged dimension and the reference dimension is extremum, and determining the one or more optical parameters of the lens based on the extremum magnification image.

Example 13 includes the subject matter of any one of Examples 9-12, and optionally, wherein the operations comprise determining at least one distance of the first distance or the second distance, based on acceleration information corresponding to an acceleration of the image capturing device.

Example 14 includes the subject matter of any one of Examples 9-13, and optionally, wherein at least one distance of the first distance or the second distance is predefined.

Example 15 includes the subject matter of any one of Examples 9-14, and optionally, wherein the operations comprise determining the first distance, based on one or more three-dimensional (3D) coordinates of the object.

Example 16 includes the subject matter of any one of Examples 9-15, and optionally, wherein the operations comprise determining the first distance based on the object and at least one dimension in the image of a calibration object having known dimensions.

Example 17 includes the subject matter of any one of Examples 9-15, and optionally, wherein the operations comprise determining the second distance based on the first distance, and one or more dimensions of a frame of the eyeglasses.

Example 18 includes the subject matter of any one of Examples 1-17, and optionally, wherein determining the one or more optical parameters comprises determining a pupillary distance between a first lens of the eyeglasses and a second lens of the eyeglasses.

Example 19 includes the subject matter of Example 18, and optionally, wherein the operations comprise processing an image of an object comprising a first element and a second element, the image comprising a first imaged element of the first element captured via the first lens and a second imaged element of the second element captured via the second lens, the operations comprising determining the pupillary distance between the first and second lenses, based on at least a first distance between the first and second elements, and a second distance between the first and second imaged elements.

Example 20 includes the subject matter of any one of Examples 1-19, and optionally, wherein the operations comprise triggering a display device to display the object.

Example 21 includes the subject matter of Example 20, and optionally, wherein the operations comprise calibrating a display size of the object on the display device.

Example 22 includes the subject matter of any one of Examples 1-21, and optionally, wherein the object comprises a circularly symmetric or rotationally symmetric object.

Example 23 includes the subject matter of any one of Examples 1-22, and optionally, wherein the operations comprise triggering an image-capturing device to capture the image of the object.

Example 24 includes a mobile device configured to determine one or more optical parameters of a lens of eyeglasses, the mobile device comprising a camera to capture at least one image of an object via the lens; and a lensometer module to determine the one or more optical parameters of the lens based on the at least one image.

Example 25 includes the subject matter of Example 24, and optionally, wherein the mobile device is configured to determine the one or more optical parameters of the lens based on a magnification between at least one imaged dimension of the object in the image and at least one respective reference dimension of the object.

Example 26 includes the subject matter of Example 25, and optionally, wherein the mobile device is configured to determine a spherical power of the lens based on the magnification.

Example 27 includes the subject matter of Example 25 or 26, and optionally, wherein the mobile device is configured to determine a cylindrical axis of the lens based on a maximal magnification axis of a plurality of axes in the image, at which a magnification between the imaged dimension and the reference dimension is maximal.

Example 28 includes the subject matter of Example 27, and optionally, wherein the mobile device is configured to determine the cylindrical power of the lens based on the maximal magnification axis and a minimal magnification axis of the plurality of axes in the image, at which a magnification between another imaged dimension and another respective reference dimension of the object is minimal.

Example 29 includes the subject matter of Example 28, and optionally, wherein the mobile device is configured to determine the cylindrical power of the lens based on a first magnification at the minimal magnification axis, and a second magnification at the maximal magnification axis.

Example 30 includes the subject matter of any one of Examples 25-29, and optionally, wherein the mobile device is configured to determine the one or more optical parameters of the lens based on the magnification, and another magnification of at least one dimension in an image of a calibration object having known dimensions, the image of the calibration object is captured not via the lens.

Example 31 includes the subject matter of any one of Examples 24-30, and optionally, wherein a distance between the object and the lens when the image is captured is half of a distance between the object and the camera when the image is captured.

Example 32 includes the subject matter of any one of Examples 24-31, and optionally, wherein the mobile device is configured to determine the one or more optical parameters of the lens based on a first distance between the object and the camera when the image is captured, and a second distance between the object and the lens when the image is captured.

Example 33 includes the subject matter of Example 32, and optionally, wherein the second distance comprises a distance between the object and the lens when temple arms of the eyeglasses are extended to a plane of the object.

Example 34 includes the subject matter of Example 32, and optionally, wherein the mobile device is configured to process a plurality of images of the object captured via the lens at a respective plurality of first distances, while the second distance is constant, to determine an extremum magnification image of the plurality of images, in which a magnification between the imaged dimension and the reference dimension is extremum, and to determine the one or more optical parameters of the lens based on the extremum magnification image.

Example 35 includes the subject matter of Example 32, and optionally, wherein the mobile device is configured to process a plurality of images of the object captured via the lens at a respective plurality of second distances, while the first distance is constant, to determine an extremum magnification image of the plurality of images, in which a magnification between the imaged dimension and the reference dimension is extremum, and to determine the one or more optical parameters of the lens based on the extremum magnification image.

Example 36 includes the subject matter of any one of Examples 32-35, and optionally, wherein the mobile device is configured to determine at least one distance of the first distance or the second distance, based on acceleration information corresponding to an acceleration of the mobile device.

Example 37 includes the subject matter of any one of Examples 32-36, and optionally, wherein at least one distance of the first distance or the second distance is predefined.

Example 38 includes the subject matter of any one of Examples 32-37, and optionally, wherein the mobile device is configured to determine the first distance, based on one or more three-dimensional (3D) coordinates of the object.

Example 39 includes the subject matter of any one of Examples 32-38, and optionally, wherein the mobile device is configured to determine the first distance based on the object and at least one dimension in the image of a calibration object having known dimensions.

Example 40 includes the subject matter of any one of Examples 32-38, and optionally, wherein the mobile device is configured to determine the second distance based on the first distance, and one or more dimensions of a frame of the eyeglasses.

Example 41 includes the subject matter of any one of Examples 24-40, and optionally, wherein determining the one or more optical parameters comprises determining a pupillary distance between a first lens of the eyeglasses and a second lens of the eyeglasses.

Example 42 includes the subject matter of Example 41, and optionally, comprising processing an image of an object comprising a first element and a second element, the image comprising a first imaged element of the first element captured via the first lens and a second imaged element of the second element captured via the second lens, the operations comprising determining the pupillary distance between the first and second lenses, based on at least a first distance between the first and second elements, and a second distance between the first and second imaged elements.

Example 43 includes the subject matter of any one of Examples 24-42, and optionally, wherein the mobile device is configured to trigger a display device to display the object.

Example 44 includes the subject matter of Example 43, and optionally, wherein the mobile device is configured to calibrate a display size of the object on the display device.

Example 45 includes the subject matter of any one of Examples 24-44, and optionally, wherein the object comprises a circularly symmetric or rotationally symmetric object.

Example 46 includes the subject matter of any one of Examples 24-45, and optionally, wherein the mobile device is configured to trigger the camera to capture the image of the object.

Example 47 includes a method of determining one or more optical parameters of a lens of eyeglasses, the method comprising processing at least one image of an object captured via the lens; and determining the one or more optical parameters of the lens based on the at least one image.

Example 48 includes the subject matter of Example 47, and optionally, comprising determining the one or more optical parameters of the lens based on a magnification between at least one imaged dimension of the object in the image and at least one respective reference dimension of the object.

Example 49 includes the subject matter of Example 48, and optionally, comprising determining a spherical power of the lens based on the magnification.

Example 50 includes the subject matter of Example 48 or 49, and optionally, comprising determining a cylindrical axis of the lens based on a maximal magnification axis of a plurality of axes in the image, at which a magnification between the imaged dimension and the reference dimension is maximal.

Example 51 includes the subject matter of Example 50, and optionally, comprising determining the cylindrical power of the lens based on the maximal magnification axis and a minimal magnification axis of the plurality of axes in the image, at which a magnification between another imaged dimension and another respective reference dimension of the object is minimal.

Example 52 includes the subject matter of Example 51, and optionally, comprising determining the cylindrical power of the lens based on a first magnification at the minimal magnification axis, and a second magnification at the maximal magnification axis.

Example 53 includes the subject matter of any one of Examples 48-52, and optionally, comprising determining the one or more optical parameters of the lens based on the magnification, and another magnification of at least one dimension in an image of a calibration object having known dimensions, the image of the calibration object is captured not via the lens.

Example 54 includes the subject matter of any one of Examples 47-53, and optionally, wherein a distance between the object and the lens when the image is captured is half of a distance between the object and an image-capturing device when the image is captured.

Example 55 includes the subject matter of any one of Examples 47-54, and optionally, comprising determining the one or more optical parameters of the lens based on a first distance between the object and an image-capturing device when the image is captured, and a second distance between the object and the lens when the image is captured.

Example 56 includes the subject matter of Example 55, and optionally, wherein the second distance comprises a distance between the object and the lens when temple arms of the eyeglasses are extended to a plane of the object.

Example 57 includes the subject matter of Example 55, and optionally, comprising processing a plurality of images of the object captured via the lens at a respective plurality of first distances, while the second distance is constant, determining an extremum magnification image of the plurality of images, in which a magnification between the imaged dimension and the reference dimension is extremum, and determining the one or more optical parameters of the lens based on the extremum magnification image.

Example 58 includes the subject matter of Example 55, and optionally, comprising processing a plurality of images of the object captured via the lens at a respective plurality of second distances, while the first distance is constant, determining an extremum magnification image of the plurality of images, in which a magnification between the imaged dimension and the reference dimension is extremum, and determining the one or more optical parameters of the lens based on the extremum magnification image.

Example 59 includes the subject matter of any one of Examples 55-58, and optionally, comprising determining at least one distance of the first distance or the second distance, based on acceleration information corresponding to an acceleration of the image capturing device.

Example 60 includes the subject matter of any one of Examples 55-59, and optionally, wherein at least one distance of the first distance or the second distance is predefined.

Example 61 includes the subject matter of any one of Examples 55-60, and optionally, comprising determining the first distance, based on one or more three-dimensional (3D) coordinates of the object.

Example 62 includes the subject matter of any one of Examples 55-61, and optionally, comprising determining the first distance based on the object and at least one dimension in the image of a calibration object having known dimensions.

Example 63 includes the subject matter of any one of Examples 55-61, and optionally, comprising determining the second distance based on the first distance, and one or more dimensions of a frame of the eyeglasses.

Example 64 includes the subject matter of any one of Examples 47-63, and optionally, wherein determining the one or more optical parameters comprises determining a pupillary distance between a first lens of the eyeglasses and a second lens of the eyeglasses.

Example 65 includes the subject matter of Example 64, and optionally, comprising processing an image of an object comprising a first element and a second element, the image comprising a first imaged element of the first element captured via the first lens and a second imaged element of the second element captured via the second lens, the operations comprising determining the pupillary distance between the first and second lenses, based on at least a first distance between the first and second elements, and a second distance between the first and second imaged elements.

Example 66 includes the subject matter of any one of Examples 47-65, and optionally, comprising triggering a display device to display the object.

Example 67 includes the subject matter of Example 66, and optionally, comprising calibrating a display size of the object on the display device.

Example 68 includes the subject matter of any one of Examples 47-67, and optionally, wherein the object comprises a circularly symmetric or rotationally symmetric object.

Example 69 includes the subject matter of any one of Examples 47-68, and optionally, comprising triggering an image-capturing device to capture the image of the object.

Example 70 includes an apparatus to determine one or more optical parameters of a lens of eyeglasses, the apparatus comprising means for processing at least one image of an object captured via the lens; and means for determining the one or more optical parameters of the lens based on the at least one image.

Example 71 includes the subject matter of Example 70, and optionally, comprising means for determining the one or more optical parameters of the lens based on a magnification between at least one imaged dimension of the object in the image and at least one respective reference dimension of the object.

Example 72 includes the subject matter of Example 71, and optionally, comprising means for determining a spherical power of the lens based on the magnification.

Example 73 includes the subject matter of Example 71 or 72, and optionally, comprising means for determining a cylindrical axis of the lens based on a maximal magnification axis of a plurality of axes in the image, at which a magnification between the imaged dimension and the reference dimension is maximal.

Example 74 includes the subject matter of Example 73, and optionally, comprising means for determining the cylindrical power of the lens based on the maximal magnification axis and a minimal magnification axis of the plurality of axes in the image, at which a magnification between another imaged dimension and another respective reference dimension of the object is minimal.

Example 75 includes the subject matter of Example 74, and optionally, comprising means for determining the cylindrical power of the lens based on a first magnification at the minimal magnification axis, and a second magnification at the maximal magnification axis.

Example 76 includes the subject matter of any one of Examples 71-75, and optionally, comprising means for determining the one or more optical parameters of the lens based on the magnification, and another magnification of at least one dimension in an image of a calibration object having known dimensions, the image of the calibration object is captured not via the lens.

Example 77 includes the subject matter of any one of Examples 70-76, and optionally, wherein a distance between the object and the lens when the image is captured is half of a distance between the object and an image-capturing device when the image is captured.

Example 78 includes the subject matter of any one of Examples 70-77, and optionally, comprising means for determining the one or more optical parameters of the lens based on a first distance between the object and an image-capturing device when the image is captured, and a second distance between the object and the lens when the image is captured.

Example 79 includes the subject matter of Example 78, and optionally, wherein the second distance comprises a distance between the object and the lens when temple arms of the eyeglasses are extended to a plane of the object.

Example 80 includes the subject matter of Example 78, and optionally, comprising means for processing a plurality of images of the object captured via the lens at a respective plurality of first distances, while the second distance is constant, determining an extremum magnification image of the plurality of images, in which a magnification between the imaged dimension and the reference dimension is extremum, and determining the one or more optical parameters of the lens based on the extremum magnification image.

Example 81 includes the subject matter of Example 78, and optionally, comprising means for processing a plurality of images of the object captured via the lens at a respective plurality of second distances, while the first distance is constant, determining an extremum magnification image of the plurality of images, in which a magnification between the imaged dimension and the reference dimension is extremum, and determining the one or more optical parameters of the lens based on the extremum magnification image.

Example 82 includes the subject matter of any one of Examples 78-81, and optionally, comprising means for determining at least one distance of the first distance or the second distance, based on acceleration information corresponding to an acceleration of the image capturing device.

Example 83 includes the subject matter of any one of Examples 78-82, and optionally, wherein at least one distance of the first distance or the second distance is predefined.

Example 84 includes the subject matter of any one of Examples 78-83, and optionally, comprising means for determining the first distance, based on one or more three-dimensional (3D) coordinates of the object.

Example 85 includes the subject matter of any one of Examples 78-84, and optionally, comprising means for determining the first distance based on the object and at least one dimension in the image of a calibration object having known dimensions.

Example 86 includes the subject matter of any one of Examples 78-84, and optionally, comprising means for determining the second distance based on the first distance, and one or more dimensions of a frame of the eyeglasses.

Example 87 includes the subject matter of any one of Examples 70-86, and optionally, wherein determining the one or more optical parameters comprises determining a pupillary distance between a first lens of the eyeglasses and a second lens of the eyeglasses.

Example 88 includes the subject matter of Example 87, and optionally, comprising means for processing an image of an object comprising a first element and a second element, the image comprising a first imaged element of the first element captured via the first lens and a second imaged element of the second element captured via the second lens, the operations comprising determining the pupillary distance between the first and second lenses, based on at least a first distance between the first and second elements, and a second distance between the first and second imaged elements.

Example 89 includes the subject matter of any one of Examples 70-88, and optionally, comprising means for triggering a display device to display the object.

Example 90 includes the subject matter of Example 89, and optionally, comprising means for calibrating a display size of the object on the display device.

Example 91 includes the subject matter of any one of Examples 70-90, and optionally, wherein the object comprises a circularly symmetric or rotationally symmetric object.

Example 92 includes the subject matter of any one of Examples 70-91, and optionally, comprising means for triggering an image-capturing device to capture the image of the object.

Functions, operations, components and/or features described herein with reference to one or more embodiments, may be combined with, or may be utilized in combination with, one or more other functions, operations, components and/or features described herein with reference to one or more other embodiments, or vice versa.

While certain features have been illustrated and described herein, many modifications, substitutions, changes, and equivalents may occur to those skilled in the art. It is, therefore, to be understood that the appended claims are intended to cover all such modifications and changes as fall within the true spirit of the disclosure.

What is claimed is:

1. A product comprising one or more tangible computer-readable non-transitory storage media comprising computer-executable instructions operable to, when executed by at least one computer processor, enable the at least one computer processor to cause a computing device to implement a lensometer to:

process, by the lensometer, an image of an object captured via a lens of eyeglasses, the image of the object captured by an image-capturing device via said lens when the lens is between the image-capturing device and the object;

determine by the lensometer a first distance, the first distance is between the image-capturing device and the object when the image of the object is captured by the image-capturing device;

determine by the lensometer a second distance, the second distance is between the lens and the object when the image of the object is captured by the image-capturing device; and determine by the lensometer one or more optical parameters of said lens based on the first distance, the second distance, and the image of the object captured via the lens.

2. The product of claim 1, wherein the instructions, when executed, cause the computing device to determine the one or more optical parameters of said lens based on a magnification between at least one imaged dimension of said object in the image and at least one respective reference dimension of said object.

3. The product of claim 2, wherein the instructions, when executed, cause the computing device to determine a spherical power of said lens based on said magnification.

4. The product of claim 2, wherein the instructions, when executed, cause the computing device to determine a cylindrical axis of said lens based on a maximal magnification axis of a plurality of axes in said image, at which a magnification between said imaged dimension and said reference dimension is maximal.

5. The product of claim 4, wherein the instructions, when executed, cause the computing device to determine a cylindrical power of said lens based on said maximal magnification axis and a minimal magnification axis of the plurality of axes in said image, at which a magnification between another imaged dimension and another respective reference dimension of said object is minimal.

6. The product of claim 5, wherein the instructions, when executed, cause the computing device to determine the cylindrical power of said lens based on a first magnification at said minimal magnification axis, and a second magnification at said maximal magnification axis.

7. The product of claim 2, wherein the instructions, when executed, cause the computing device to determine the one or more optical parameters of said lens based on said magnification, and another magnification of at least one dimension in an image of a calibration object having known dimensions, the image of the calibration object is captured not via the lens.

8. The product of claim 1, wherein the second distance is half of the first distance.

9. The product of claim 1, wherein the instructions, when executed, cause the computing device to process an image of a graphical display comprising a first object and a second object, the image of the graphical display comprising a first image of the first object captured by the image-capturing device via the lens, and a second image of the second object captured by the image-capturing device not via the lens, the instructions, when executed, cause the computing device to determine at least one of the first distance and the second distance based on the second image of the second object, and to determine the one or more optical parameters of said lens based on the first image of the first object.

10. The product of claim 1, wherein the second distance comprises a distance between said object and said lens when temple arms of said eyeglasses are extended to a plane of said object.

11. The product of claim 1, wherein the instructions, when executed, cause the computing device to process a plurality of images of said object captured via said lens at a respective plurality of first distances, while the second distance is constant, to determine an extremum magnification image of said plurality of images, in which a magnification between an imaged dimension of the object and a reference dimension of the object is extremum, and to determine the one or more optical parameters of said lens based on said extremum magnification image.

12. The product of claim 1, wherein the instructions, when executed, cause the computing device to process a plurality of images of said object captured via said lens at a respective plurality of second distances, while the first distance is constant, to determine an extremum magnification image of said plurality of images, in which a magnification between an imaged dimension of the object and a reference dimension of the object is extremum, and to determine the one or more optical parameters of said lens based on said extremum magnification image.

13. The product of claim 1, wherein the instructions, when executed, cause the computing device to determine at least one distance of the first distance or the second distance, based on acceleration information corresponding to an acceleration of said image-capturing device.

14. The product of claim 1, wherein the instructions, when executed, cause the computing device to instruct a user to place the image-capturing device and the lens such that a distance between the image-capturing device and the lens is half of the first distance.

15. The product of claim 1, wherein the instructions, when executed, cause the computing device to determine the first distance, based on one or more three-dimensional (3D) coordinates of said object.

16. The product of claim 1, wherein the instructions, when executed, cause the computing device to determine the first distance based on said object and at least one dimension in said image of a calibration object having known dimensions.

17. The product of claim 1, wherein the instructions, when executed, cause the computing device to determine the second distance based on said first distance, and one or more dimensions of a frame of said eyeglasses.

18. The product of claim 1, wherein the instructions, when executed, cause the computing device to determine a pupillary distance between a first lens of said eyeglasses and a second lens of said eyeglasses.

19. The product of claim 18, wherein the instructions, when executed, cause the computing device to process an image of an object comprising a first element and a second element, the image comprising a first imaged element of said first element captured via said first lens and a second imaged element of said second element captured via said second lens; and to determine the pupillary distance between said first and second lenses, based on at least a first distance between said first and second elements, and a second distance between said first imaged element and said second imaged element.

20. The product of claim 1, wherein the instructions, when executed, cause the computing device to trigger a display device to display said object.

21. The product of claim 20, wherein instructions, when executed, cause the computing device to calibrate a display size of said object on said display device.

22. The product of claim 1, wherein the object comprises a circularly symmetric or rotationally symmetric object.

23. The product of claim 1, wherein the instructions, when executed, cause the computing device to trigger the image-capturing device to capture the image of said object.

24. A mobile device configured to determine one or more optical parameters of a lens of eyeglasses, the mobile device comprising:
 an image-capturing device to capture an image of an object via said lens when the lens is between the image-capturing device and the object; and
 a lensometer configured to:
  determine a first distance, the first distance is between the image-capturing device and the object when the image of the object is captured by the image-capturing device;
  determine a second distance, the second distance is between the lens and the object when the image of the object is captured by the image-capturing device; and
  determine the one or more optical parameters of said lens based on the first distance, the second distance, and the image of the object captured via the lens.

25. The mobile device of claim 24 configured to determine the one or more optical parameters of said lens based on a magnification between at least one imaged dimension of said object in the image and at least one respective reference dimension of said object.

26. The mobile device of claim 24, wherein the lensometer is configured to process an image of a graphical display comprising a first object and a second object, the image of the graphical display comprising a first image of the first object captured by the image-capturing device via the lens, and a second image of the second object captured by the image-capturing device not via the lens; to determine at least one of the first distance and the second distance based on the second image of the second object; and to determine the one or more optical parameters of said lens based on the first image of the first object.

27. The mobile device of claim 24 configured to determine at least one of the first distance and the second distance based on the image captured by the image-capturing device.

28. The product of claim 1, wherein the instructions, when executed, cause the computing device to determine at least one of the first distance and the second distance based on sensor information from a sensor.

29. A method to be performed by a lensometer implemented by a computing device, the method comprising:
 processing by the lensometer an image of an object captured via a lens of eyeglasses, the image of the object captured by an image-capturing device via said lens when the lens is between the image-capturing device and the object;
 determining by the lensometer a first distance, the first distance is between the image-capturing device and the object when the image of the object is captured by the image-capturing device;
 determining by the lensometer a second distance, the second distance is between the lens and the object when the image of the object is captured by the image-capturing device; and
 determining by the lensometer one or more optical parameters of said lens based on the first distance, the second distance, and the image of the object captured via the lens.

30. The method of claim 29 comprising determining the one or more optical parameters of said lens based on a magnification between at least one imaged dimension of said object in the image and at least one respective reference dimension of said object.

* * * * *